United States Patent
Toor

(10) Patent No.: US 12,076,080 B2
(45) Date of Patent: Sep. 3, 2024

(54) COMPACT LASER SCALPEL AND METHOD FOR PREFERENTIAL ABLATION OF TUMOR TISSUE

(71) Applicant: UNIVERSITY OF IOWA RESEARCH FOUNDATION, Iowa City, IA (US)

(72) Inventor: Fatima Toor, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 17/338,395

(22) Filed: Jun. 3, 2021

(65) Prior Publication Data

US 2021/0378742 A1 Dec. 9, 2021

Related U.S. Application Data

(60) Provisional application No. 63/034,904, filed on Jun. 4, 2020.

(51) Int. Cl.
*A61B 18/20* (2006.01)
*A61B 18/22* (2006.01)
(Continued)

(52) U.S. Cl.
CPC .............. *A61B 18/22* (2013.01); *A61B 90/36* (2016.02); *H01S 5/3401* (2013.01); *A61B 2018/00577* (2013.01); *A61B 2018/2015* (2013.01); *A61B 2018/2035* (2013.01); *A61B 2018/2233* (2013.01)

(58) Field of Classification Search
CPC ................................ A61B 18/20; A61N 5/06
See application file for complete search history.

(56) References Cited

U.S. PATENT DOCUMENTS 4,458,683 A * 7/1984 Saito ...................... A61B 18/22
606/3
6,084,242 A * 7/2000 Brown, Jr. ........... A61N 5/0616
250/504 R
(Continued)

OTHER PUBLICATIONS

Katta et al., "Laser brain cancer surgery in a xenograft model guided by optical coherence tomography", May 26, 2019, Theranostics 2019, vol. 9, Issue 12, pp. 3555-3564 (Year: 2019).*
(Continued)

*Primary Examiner* — Lynsey C Eiseman
(74) *Attorney, Agent, or Firm* — Viksnins Harris Padys Malen LLP

(57) ABSTRACT

An apparatus and method of treatment of an animal using the apparatus are disclosed. The apparatus includes a scalpel, a laser included in the scalpel, and a visible light source included in the scalpel. The visible light source provides a visible targeting beam. The method of treatment includes activating a visible targeting beam in a laser scalpel. The visible targeting beam has an illumination intensity. The method further includes illuminating a tumor that includes cancerous cells and non-cancerous cells with the visible targeting beam, activating an invisible mid-infrared laser included in the scalpel to produce a laser spot at the tumor, and ablating the cancerous cells while leaving the non-cancerous cells substantially undamaged.

4 Claims, 18 Drawing Sheets
(2 of 18 Drawing Sheet(s) Filed in Color)

(51) Int. Cl.
A61B 90/00 (2016.01)
H01S 5/34 (2006.01)
A61B 18/00 (2006.01)

(56) References Cited

U.S. PATENT DOCUMENTS

| | | | |
|---|---|---|---|
| 6,129,723 | A | 10/2000 | Anderson et al. |
| 7,630,418 | B2 | 12/2009 | Franjic et al. |
| 8,074,661 | B2 | 12/2011 | Hutson et al. |
| 8,202,268 | B1* | 6/2012 | Wells ............... A61B 18/22 606/9 |
| 2003/0144654 | A1* | 7/2003 | Hilal ............... A61B 18/20 606/34 |
| 2003/0187325 | A1 | 10/2003 | Meister et al. |
| 2007/0060984 | A1* | 3/2007 | Webb ............... A61N 5/0622 607/89 |
| 2011/0087202 | A1* | 4/2011 | Lewinsky ......... A61N 5/0603 606/14 |
| 2011/0306956 | A1* | 12/2011 | Islam ............... A61B 18/20 606/14 |
| 2014/0350534 | A1 | 11/2014 | Kircher et al. |
| 2016/0317228 | A1 | 11/2016 | Fermann et al. |
| 2018/0055690 | A1 | 3/2018 | Miller et al. |

OTHER PUBLICATIONS

Abramov, P , et al., "Quantum-Cascade Lasers in Medicine and Biology (Review)", Journal of Applied Spectroscopy, 86 (1), 1-26, (Mar. 2019) (Russian Original vol. 86, No. 1, Jan.-Feb. 2019).

Akalin, A , et al., "Classification of malignant and benign tumors of the lung by infrared spectral histopathology (SHP)", Lab Invest 95 (4), 406-421 (2015).

Ali, H , et al., "Infrared spectroscopic analysis of skin tumor of mice treated with several medicinal plants", Asian Pacific Journal of Tropical Disease 3 (5), 405-408 (2013).

Anastassopoulou, J , et al., "Microimaging FT-IR spectroscopy on pathological breast tissues", Vibrational Spectroscopy 51 (2), 270-275 (2009).

Auner, G , et al., "Applications of Raman spectroscopy in cancer diagnosis", Cancer Metastasis Rev 37 (4), 691-717 (2018).

Awazu, K , et al., "Infrared Laser Therapy using IR absorption of biomolecules", 3rd International Photonics & OptoElectronics Meetings (POEM 2010); Journal of Physics: Conference Series 276, 012011, 9 pages (2011).

Barroso, E , et al., "Discrimination between oral cancer and healthy tissue based on water content determined by Raman spectroscopy", Anal Chem 87 (4), 2419-2426 (2015).

Barth, A , "Infrared spectroscopy of proteins", Biochimica et Biophysica Acta (BBA)—Bioenergetics 1767(9), 1073-1101 (2007).

Barth, A , et al., "What vibrations tell US about proteins", Quarterly Reviews of Biophysics 35 (4), 369-430 (2002).

Benard, A , et al., "Discrimination between healthy and tumor tissues on formalin-fixed paraffin-embedded breast cancer samples using IR imaging", Spectroscopy 24, 67-72 (2010).

Blum, J , et al., "Distinct and overlapping sarcoma subtypes initiated from muscle stem and progenitor cells", Cell Rep 5(4), 933-940 (2013).

Brancaleon, L , et al., "Attenuated total reflection-Fourier transform infrared spectroscopy as a possible method to investigate biophysical parameters of stratum corneum in vivo", J Invest Dermatol 116 (3), 380-386 (2001).

Capelli, M , et al., "CO2 Laser in the Treatment of Laryngeal Synovial Sarcoma: A Clinical Case", Tumori 93, 296-299 (2007).

Dritsa, V , et al., "An infrared spectroscopic study of aortic valve. A possible mechanism of calcification and the role of magnesium salts", In Vivo 28 (1), 91-98 (2014).

Hashimura, K , et al., "Selective removal of atherosclerotic plaque with a quantum cascade laser in the 5.7μm wavelength range", Japanese Journal of Applied Physics 54, 112701-1-112701-6 (2015).

Jean, B , et al., "Mid-IR Laser Applications in Medicine", I.T. Sorokina, K.L. Vodopyanov (Eds.): Solid-State Mid-Infrared Laser Sources, Topics Appl. Phys. 89, 511-546 (2003).

Ke, K , et al., "Mid-infrared absorption spectroscopy and differential damage in vitro between lipids and proteins by an all-fiber-integrated supercontinuum laser", Opt Express 17 (15), 12627-12640 (2009).

Kim, M , et al., "High-power continuous-wave interband cascade lasers with 10 active stages", Optics Express 23 (8), 9664-9672 (2015).

Kyriakidou, M , et al., "An FT-IR Spectral Analysis of the Effects of γ-Radiation on Normal and Cancerous Cartilage", In Vivo 30 (5), 599-604 (2016).

Kyriakidou, M , et al., "FT-IR Spectroscopy Study in Early Diagnosis of Skin Cancer", In Vivo 31(6), 1131-1137 (2017).

Larson, E , et al., "Mid-infrared absorption by soft tissue sarcoma and cell ablation utilizing a mid-infrared interband cascade laser", J Biomed Opt 26(4), 043012-1-043012-10 (2021).

Lyng, F , et al., "Vibrational Microspectroscopy for Cancer Screening", Appl. Sci. 5(1), 23-35; https://doi.org/10.3390/app5010023 (2015).

Mackanos, M , et al., "Mid infrared optical parametric oscillator (OPO) as a viable alternative to tissue ablation with the free electron laser (FEL)", Lasers Surg Med 39 (3), 230-236 (2007).

Masaki, N , et al., "Selective delivery of laser energy to ester bonds of triacylglycerol in lipid droplets of adipocyte using a quantum cascade laser", Biomedical Optics Express 9 (5), 2095-2103 pages (2018).

Mavrogenis, A , et al., "Fourier transform infrared spectroscopic studies of radiation-induced molecular changes in bone and cartilage", Expert Review of Quality of Life in Cancer Care 1 (6), (2016).

Mehrotra, R , et al., "Analysis of ovarian tumor pathology by Fourier Transform Infrared Spectroscopy", J Ovarian Res 3 (27) 1-6 (2010).

Mirov, S , et al., "Frontiers of Mid-IR Lasers Based on Transition Metal Doped Chalcogenides", IEEE Journal of Selected Topics in Quantum Electronics 24 (5), 1601829 , 29 pages (Sep./Oct. 2018).

Palesty, J , et al., "Nd:YAG laser surgery for the excision of pilonidal cysts: a comparison with traditional techniques", Lasers Surg Med 26(4), 380-385 (2000).

Rothman, L , et al., "The HITRAN2012 molecular spectroscopic database", Journal of Quantitative Spectroscopy and Radiative Transfer 130, 4-50 (2013).

Seddon, A , "Potential for using mid-infrared light for non-invasive, early-detection of skin cancers in vivo", Proc of SPIE 8576, 85760V-1-85760V-10 (2013).

Serebryakov, V , et al., "Mid-IR laser for high-precision surgery", J Opt Technol 82 (12), 781-788 (2015).

Snyder, R , et al., "Vibrational spectra in the C殳H stretching region and the structure of the polymethylene chain", Spectrochimica Acta Part A: Molecular Spectroscopy 34 (4), 395-406 (1978).

Su, K , et al., "Fourier Transform Infrared Spectroscopy as a Cancer Screening and Diagnostic Tool: A Review and Prospects", Cancers 12, 115, doi:10.3390/cancers12010115, 1-19 (2020).

Warren, S , et al., "Optical constants of ice from the ultraviolet to the microwave: A revised compilation", Journal of Geophysical Research: Atmospheres 113 (D14) (2008).

Wehbe, K , et al., "Differentiation between normal and tumor vasculature of animal and human glioma by FTIR imaging", Analyst 135 (12), 3052-3059 (2010).

Xiao, Y , et al., "Wavelength-Dependent Collagen Fragmentation during Mid-IR Laser Ablation", Biophys J 91 (4), 1424-1432 (2006).

Yang, R , et al., "Infrared laser based on intersubband transitions in quantum wells", Superlattices and Microstructures 17 (1), 77-83 (1995).

Yao, H , et al., "The Use of FTIR-ATR Spectrometry for Evaluation of Surgical Resection Margin in Colorectal Cancer: A Pilot Study of 56 Samples", J. Spectrosc. 2014, Article ID 213890, 4 pages (2014).

(56) References Cited

OTHER PUBLICATIONS

Zohdi, V , et al., "Importance of Tissue Preparation Methods in FTIR Micro-Spectroscopical Analysis of Biological Tissues: 'Traps for New Users'", PLoS 10(2), e0116491, 1-11 (2015).

* cited by examiner

| Subject ID | Sex | Current Mortality Status | Diagnosis | Year of Diagnosis | Age at Diagnosis | Year of Surgical Procedure | Type of Tissue | Anatomical Location | Pathological Analysis of Resected Tissue |
|---|---|---|---|---|---|---|---|---|---|
| MS1543 | F | Cease to Breathe (2015) | High grade sarcoma with features of myxofibrosarcoma and pleomorphic liposarcoma | 2014 | 58 | 2014 | Soft | Hip & thigh (upper leg) | 100% tumor |
| MS1722 | F | Alive | Myxofibrosarcoma | 2015 | 63 | 2015 | Soft | Elbow & forearm | 100% tumor |
| S10097 | M | Alive | Dermatofibrosarcoma protuberans | 2016 | 47 | 2017 | Soft | Shoulder | 80% tumor |
| MS1932 | M | Alive | Myxofibrosarcoma | 2016 | 66 | 2016 | Soft | Leg-Lower (shin, calf) | 66% tumor |
| MS1689 | M | Alive | Myxofibrosarcoma | 2015 | 62 | 2015 | Soft | Leg-Upper, thigh | 100% tumor |
| S10099 | M | Alive | Myxofibrosarcoma | 2017 | 48 | 2017 | Soft | Elbow & forearm | 100% tumor |

FIG. 18

COMPACT LASER SCALPEL AND METHOD FOR PREFERENTIAL ABLATION OF TUMOR TISSUE

RELATED APPLICATION

This application claims priority to U.S. Provisional Patent Application No. 63/034,904 that was filed on Jun. 4, 2020. The entire content of the application referenced above is hereby incorporated by reference herein.

BACKGROUND

The present disclosure relates to an apparatus and method for use in laser surgery. Researchers and medical professionals have utilized bulky, expensive laser light sources for surgical applications. These laser light sources are typically housed in a room separated from the operating room or in a large containment within the operating room. The handheld surgical devices that are connected to these laser light sources are awkward to wield and experience transmission line losses as the light travels from the laser to the handheld device. Aspects of the disclosed embodiments address these and other disadvantages and concerns associated with laser surgery.

SUMMARY

Consistent with the disclosed embodiments, an apparatus of manufacture comprises a scalpel, a laser included in the scalpel, and a visible light source included in the scalpel. The visible light source provides a visible targeting beam for the laser. In some embodiments, the laser has a length of between about two millimeters and about five millimeters. In some embodiments, the laser has a laser beam having a wavelength of between about three microns and about six microns. In some embodiments, the laser has a power of between about one-half watt and two watts. In some embodiments, the laser beam has a spot size having a diameter of between about ten microns and about one hundred microns. In some embodiments, the laser beam, the laser power, the laser's operational pulse width and frequency, and the spot size are computer controllable. In some embodiments, the laser provides a beam having a wavelength of about three microns. In some embodiments, the laser is a cascaded superlattice laser. In some embodiments, the laser provides a beam having a wavelength of about six microns. In some embodiments, the laser is a quantum cascade laser or a cascaded superlattice laser. In some embodiments, the laser includes two mid-infrared lasers. In some embodiments, the laser is a surface emitting mid-infrared laser. In some embodiments, the laser is an edge emitting mid-infrared lasers. In some embodiments, one of the two lasers is a quantum cascade laser. In some embodiments, the laser includes a beam and the beam has a duty cycle of between about 0.1 percent and about one percent for frequencies between about one hundred hertz and about one kilohertz. In some embodiments, the apparatus further comprises a laser controller included in the scalpel handle and coupled to the laser. In some embodiments, the laser controller includes hand-activated controls located on the scalpel for controlling one or more characteristics of the laser. In some embodiments, the apparatus further comprises a controller for controlling an optical system coupled to the laser. In some embodiments, the apparatus further comprises a robot arm coupled to the scalpel.

Consistent with the disclosed embodiments, a method of treatment of an animal disclosed. The method comprises activating a visible targeting beam in a laser scalpel, the visible targeting beam having an illumination intensity. The method further comprises illuminating a tumor that includes cancerous cells and non-cancerous cells with the visible targeting beam. The method further comprises activating an invisible mid-infrared laser included in the scalpel to produce a laser spot at the tumor. And the method further comprises ablating the cancerous cells while leaving the non-cancerous cells substantially undamaged. In some embodiments, activating the visible targeting beam in the laser scalpel comprises activating a beam activation control in the scalpel to activate the visible targeting beam. In some embodiments, illuminating the tumor that includes cancerous cells and non-cancerous cells with the visible targeting beam comprises controlling the illumination intensity through an illumination intensity control located in the scalpel. In some embodiments, activating the invisible mid-infrared laser included in the scalpel to produce the laser spot at the tumor comprises activating a laser activation control in the scalpel to activate the laser. In some embodiments, activating the invisible mid-infrared laser included in the scalpel to produce the laser spot at the tumor comprises activating a predefined tumor exposure profile to control the laser. In some embodiments, ablating the cancerous cells while leaving the non-cancerous cells undamaged comprises controlling one or more characteristics of the laser spot. In some embodiments, the animal is a mammal. In some embodiments, the mammal is a human. In some embodiments, the cancerous cells are sarcoma cells. In some embodiments, the laser spot has a wavelength of about three or about six microns.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 18 shows a patient Table including patient demographics, diagnosis, type of tissue, and anatomical location of the cancer in accordance with some embodiments of the present disclosure.

DESCRIPTION

Reference will now be made in detail to the embodiments implemented according to this disclosure, the examples of which are illustrated in the accompanying drawings.

Figure 1:
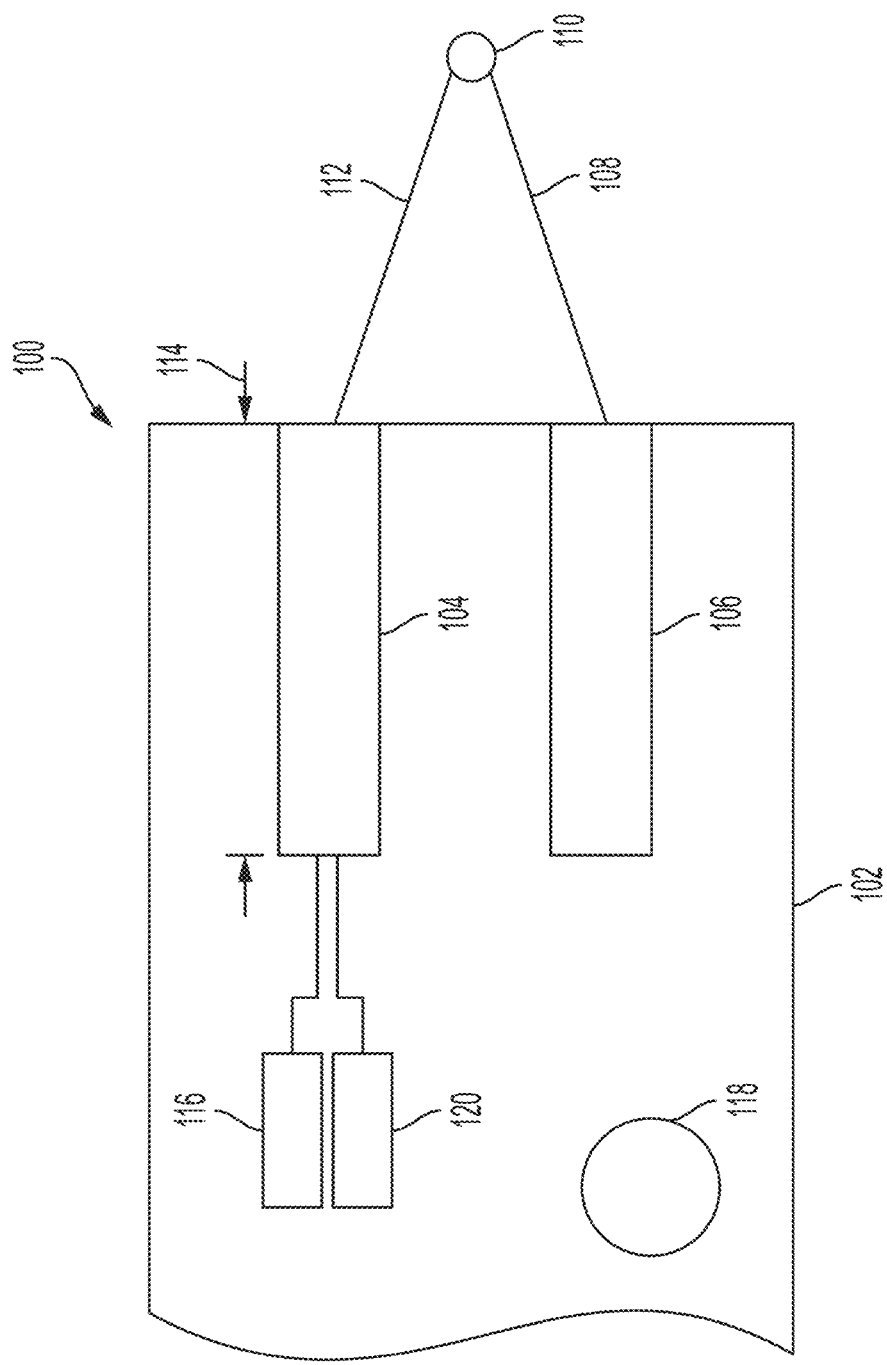
FIG. 1 shows an illustration of an apparatus including a scalpel, a laser included in the scalpel, and a visible light source included in the scalpel in accordance with some embodiments of the present disclosure.

FIG. 1 shows an illustration of an apparatus 100 including a scalpel 102, a laser 104 included in the scalpel 102, and a visible light source 106 included in the scalpel 102 in accordance with some embodiments of the present disclosure. The visible light source 106, in operation, provides a visible targeting beam 108 to illuminate an ablation target 110, such as a tumor. The laser 104, in operation, provides a laser beam 112 to ablate the ablation target 110. The ablation target 110 is typically a cancerous tumor. The scalpel 102 is designed to be handheld or coupled to a robot arm.

The laser 104 has a compact form factor that permits the laser 104 to be included in the scalpel 102. In some embodiments, the laser 104 has a length 114 of between about two and about five millimeters. In some embodiments, the laser 104 has a thickness of about ten micrometers and a width of about ten micrometers. An example laser 104 can be epitaxially grown on a three-hundred to five-hundred micrometer thick InP or GaSb substrate. The properties of the laser 104 are selected for use in the preferential ablation of cancer cells. In some embodiments, the laser beam 112 has a wavelength of between about three microns and about six microns. In some embodiments, the wavelength of the laser beam 112 is about three microns. A laser beam 112 having a wavelength of about three microns is useful in the selective ablation of sarcoma cancer cells and melanoma cancer cells. In some embodiments, the wavelength of the laser beam 112 is about six microns. A laser beam 112 having a wavelength of about six microns is useful in the selective ablation of melanoma cancer cells and sarcoma cancer cells. In some embodiments, the laser beam 112 has a duty cycle of between about 0.1 percent and about 1 percent for frequencies between about one hundred hertz and about one kilohertz. A duty cycle is selected for the effective ablation of particular types of cancer cells or tumors. A power suitable for use in the selective ablation of cancer cells is between about one-half and about two watts. In some embodiments, the laser beam 112 has a spot size having a diameter of between about ten microns and about one hundred microns. In some embodiments, the laser beam 112, the wavelength of the laser beam 112, the laser power, and the spot size are computer controllable.

The laser 104 is not limited to a particular type of laser. Example lasers having properties suitable for us as the laser 104 in the apparatus 100 include cascaded superlattice lasers and quantum cascade lasers. A quantum cascade laser is a semiconductor laser that emits in the mid-infrared to far-infrared portion of the electromagnetic spectrum. A mid-infrared laser emits radiation having wavelengths ranging from about three micrometers to about eight micrometers. The mid-infrared region of the electromagnetic spectrum is the most attractive spectral region for ablation of both soft and hard tissues because molecules such as water, proteins, and lipids that are contained in biological tissue strongly absorb mid-infrared electromagnetic radiation. Mid-infrared laser ablation and excision of tissue during surgery can improve patient care: (i) laser excision causes less damage to neighboring tissue than metallic blades and can be applied to more sensitive structures, (ii) the heat produced by a laser helps sterilize the edges of the tissue that it's cutting, reducing the risk of infection, (iii) since laser heat coagulates blood vessels, there is often less bleeding, swelling, pain, or scarring, and (iv) healing time is often shorter because of less damage to healthy tissue during laser excision. A superlattice laser is based on interband laser transitions that occur in a series of quantum wells, made of group III-V semiconductors, designed for carrier injection into and ejection out of the laser transition energy levels. The series of quantum wells is called the superlattice and it can be cascaded several times so that each electron-hole pair generates several photons resulting in high power laser output. The laser 104 can be configured to include two or more lasers. In some embodiments, the laser 104 includes two mid-infrared lasers. In some embodiments, one of the two lasers is a quantum cascade laser.

In some embodiments, the apparatus 100 further includes a laser controller 116 included in the scalpel 102 and coupled to the laser 104. In some embodiments, the laser controller 116 includes hand-activated controls 118 included in the scalpel 102 for controlling one or more characteristics of the laser 104. In some embodiments, the apparatus 100 further includes a optics controller 120 for controlling an optical system coupled to the laser.

The visible light source 106 is not limited to a particular source of visible light. In some embodiments, the visible light source 106 includes a visible light emitting diode. The visible targeting beam 108 is aligned with the laser beam 112 such that the visible targeting beam 108 illuminates an ablation target. Alignment of the laser beam 112 with the visible targeting beam 108 means the laser beam 112 is directed to the ablation target 110 illuminated by the visible targeting beam 108.

In operation, a surgeon manipulates the apparatus 100 to illuminate the ablation target 110 with the visible targeting beam 108 of the apparatus 100 and then activates the laser 104 to selectively ablate the cancer cells included in the ablation target 110. Example ablation targets include tumors, such as cancerous tumors, including sarcoma tumors and melanoma tumors.

Figure 2:
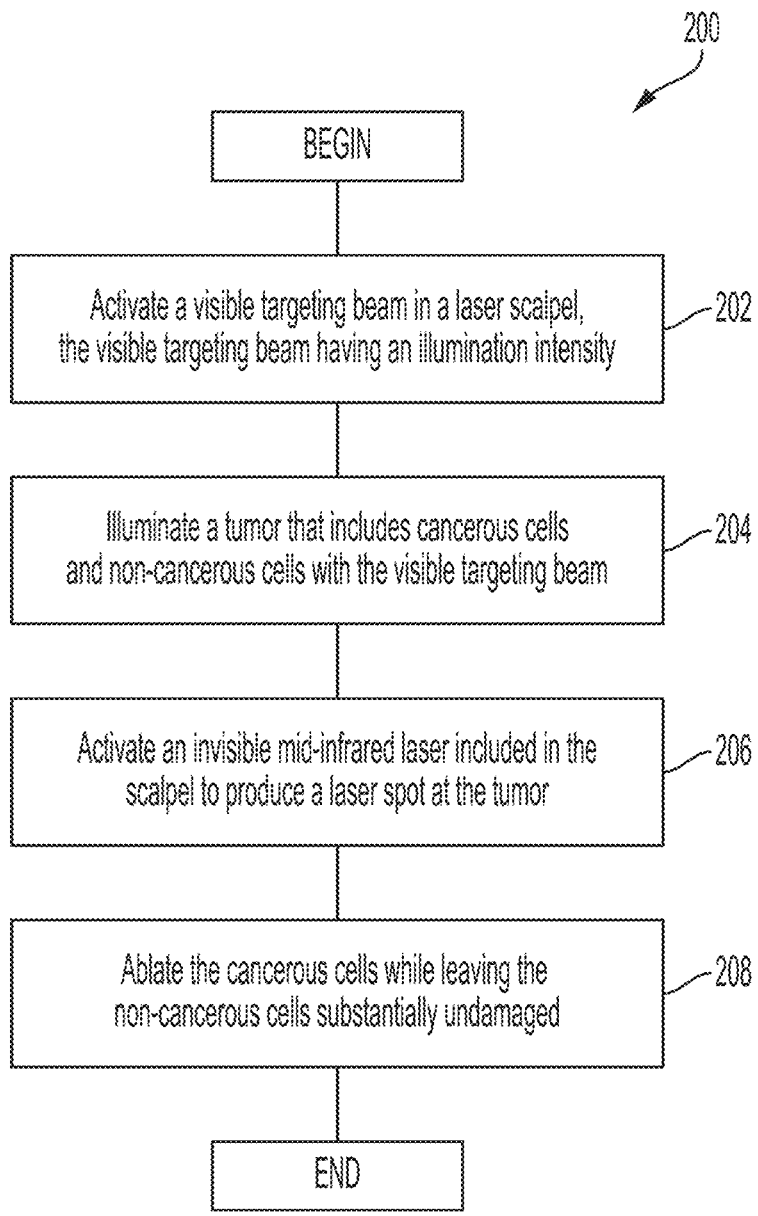
FIG. 2 shows a flow diagram for a method of treatment for an animal in accordance with some embodiments of the present disclosure.

FIG. 2 shows a flow diagram 200 for a method of treatment of an animal in accordance with some embodiments of the present disclosure. The method 200 includes activating a visible targeting beam in a laser scalpel, the visible targeting beam having an illumination intensity (block 202), illuminating a tumor that includes cancerous cells and non-cancerous cells with the visible targeting beam (block 204), activating an invisible mid-infrared laser included in the scalpel to produce a laser spot at the tumor (block 206), and ablating the cancerous cells while leaving the non-cancerous cells substantially undamaged (block 208).

The activation of the visible targeting beam is not limited to a particular method of activation. In some embodiments, activating the visible targeting beam in the laser scalpel includes activating a beam activation control in the scalpel to activate the visible targeting beam. The illumination of the tumor can be controlled. In some embodiments, illuminating the tumor that includes cancerous cells and non-cancerous cells with the visible targeting beam includes controlling the illumination intensity through an illumination intensity control located in the scalpel. Activation of the invisible mid-infrared laser can also be controlled. In some embodiments, activating the invisible mid-infrared laser included in the scalpel to produce the laser spot at the tumor includes activating a laser activation control in the scalpel to activate the laser. The invisible mid-infrared laser can also be automatically controlled and tuned to a particular cancer. In some embodiments, activating the invisible mid-infrared laser included in the scalpel to produce the laser spot at the tumor includes activating a predefined tumor exposure profile to control the laser. The method can be further controlled and tuned to target particular cancers. In some embodiments, ablating the cancerous cells while leaving the non-cancerous cells undamaged includes controlling one or more characteristics of the laser spot.

The method shown in the flow diagram 200 is useful for treatment of cancers in different types of animals. In some embodiments, the animal is a mammal. In some embodiments, the mammal is a human. In some embodiments, the cancerous cells are sarcoma cells. In some embodiments, the cancerous cells are melanoma cells.

Experiments have shown unexpectedly that primary undifferentiated pleomorphic sarcoma cancer cells can be killed with milli-watt power levels at low density while at higher cell density, higher power lasers are needed. Further, using Fourier transform infrared spectroscopy of human tissues obtained from sarcoma patients the inventors discovered that tumor tissue has higher absorption than neighboring healthy tissue at about three micrometers. This result was unexpected. Utilizing this data, the inventors conducted studies on a cancer cell line (C1619) to study the efficacy of a relatively low power (30 mW) interband cascade laser in ablating cell lines. The inventors demonstrated that the interband cascade laser is effectively able to ablate cells with low density (1000 cells per well). The data indicates that three and six micrometer wavelengths are highly efficient at ablating soft tissue photo-thermally with very low ablation thresholds. Therefore, hundreds of milli-watts is sufficient power to ablate tumors and tissues. This differential absorption enables preferential ablation of the tumor using mid-infrared lasers. Mid-infrared laser based ablation of cancer cells results in cancer cell death at milliwatt level mid-infrared radiation power. Experiments showed for six patients that there is higher absorption of tumor tissue in the 2.8 μm to 3.6 μm wavelengths.

Figure 3:
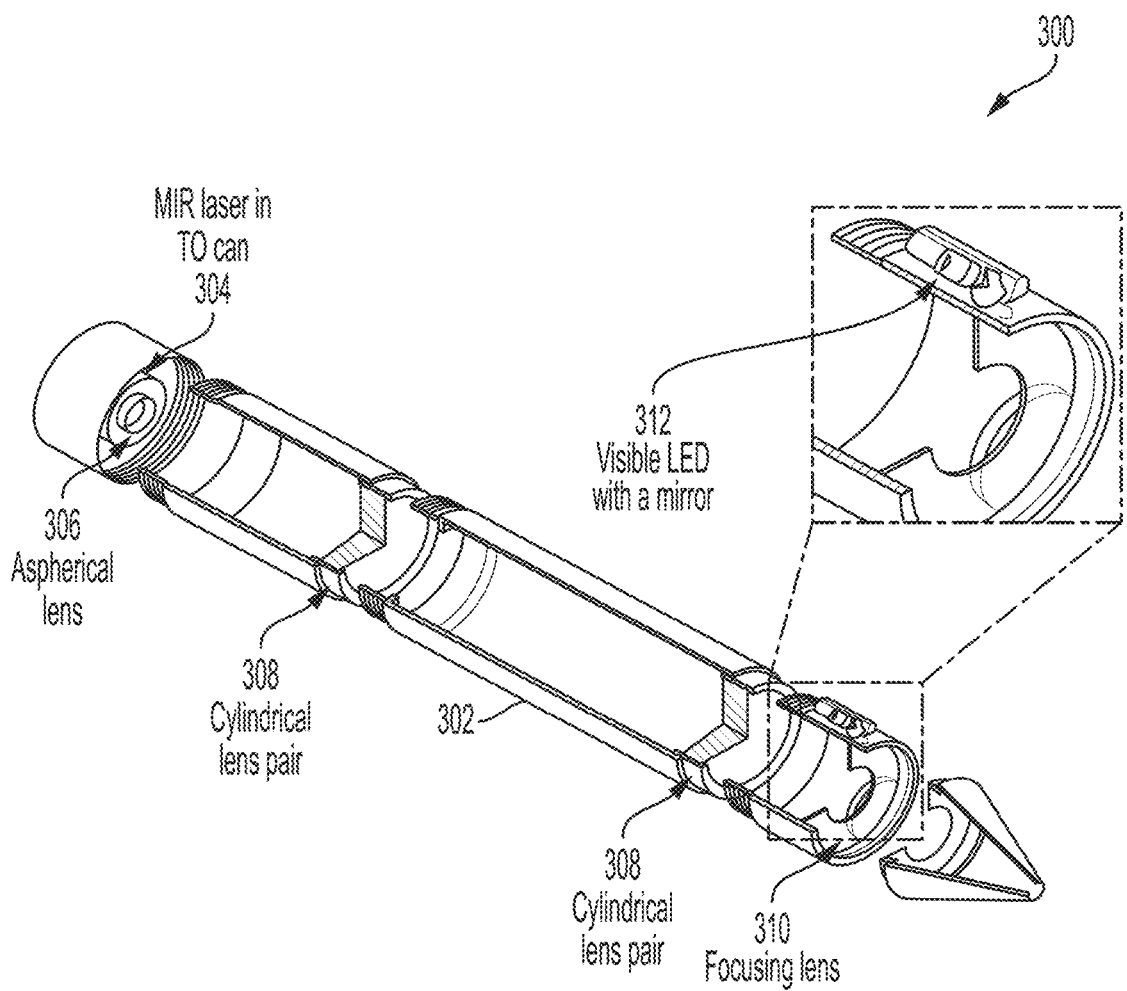
FIG. 3 shows an illustration of an apparatus including a laser scalpel, a mid-infrared laser with an aspherical lens, a cylindrical lens pair, a focusing lens, and a visible light-emitting diode and a mirror in accordance with some embodiments of the present disclosure.

FIG. 3 shows an illustration of an apparatus 300 including a laser scalpel 302, a mid-infrared laser 304 with an aspherical lens 306, a cylindrical lens pair 308, a focusing lens 310, and a visible light-emitting diode with a mirror system 312.

The initial output of a laser diode is not fully collimated due to diffraction from the small cavity cross section; however, this is overcome by placing either a parabolic mirror pair or aspherical lens in front of the diode. For an aspherical lens, the precisely molded shape of the lens collimates the light. The numerical aperture (NA) of the aspherical lens is approximately 2× that of the laser. Another specification of the selected lens is transparency to mid-IR (MIR) light which should be at least 90% for 3 to 6 micron MIR wavelengths.

The laser beam should be circularized to avoid astigmatic focusing. The emission of the laser has an elliptical shaped output due to the difference in fast and slow axis. To change the output beam shape, a pair of anamorphic prisms or a pair of cylindrical lenses can be used. A pair of high-transparency calcium fluoride ($CaF_2$) cylindrical lenses to circularize the laser beam output can be used with typical 95% transparency in the MIR. The choice of lenses is based on the ratio between the focal length of the two lenses using the following equation $$\theta_{fast} = \theta_{slow} * \frac{f_2}{f_1}.$$

Rearranging to get $$\frac{\theta_{fast}}{\theta_{slow}} = \frac{f_2}{f_1} \rightarrow \frac{55}{30} = \frac{f_2}{f_1} \rightarrow \frac{f_2}{f_1} = 1.833,$$

this is the required ratio to circularize the output.

The laser beam is focused to maximize the beam irradiance for cancer tissue and cell ablation. In some embodiments, a spot size of ~12 microns is used with a f=4.80 mm focal length ZnSe lens. The focused spot according to Gaussian beam optics is:

$$w_0 = \frac{2M^2 \lambda f}{\pi D} \approx \frac{2(1.3)(3.3 \; \mu m)(4.8 \; mm)}{\pi (2.2 \; mm)} \approx 6 \; \mu m,$$

where $w_0$ is the beam waist, $M^2$ is the beam quality factor, f is the lens focal length, and D is the beam diameter before the lens.

Each of the lenses is placed at a specific distance in the laser scalpel package from each other to achieve the desired outcome. The overall diameter of the scalpel is constrained by the cylindrical lenses because they are the largest pieces that need to fit into the housing. The laser scalpel can be designed and modeled engineering design software with the intent of getting the parts 3D-printed in aluminum. In some embodiments, five pieces screw together and clamp the lenses into place for the final product. The visible LED coupled with a mirror is integrated outside the optical cavity of the scalpel. The design is compact and lightweight, and thus suitable for a handheld device.

Figure 4:
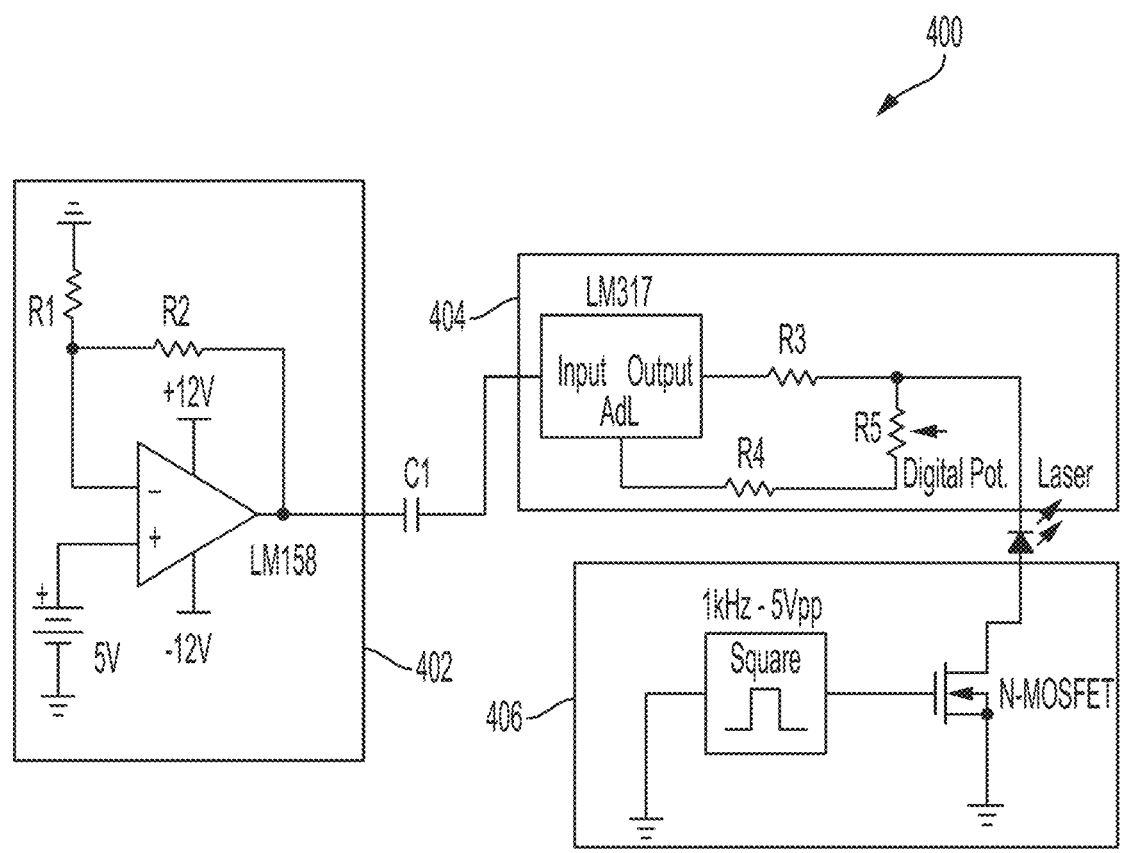
FIG. 4 shows an illustration of a schematic diagram of circuit for driving the laser scalpel shown in FIG. 3 in accordance with some embodiments of the present disclosure.

FIG. 4 shows an illustration of a schematic diagram 400 of drive electronics for driving the electronics included in the laser scalpel 302 shown in FIG. 3 in accordance with some embodiments of the present disclosure. The drive electronics shown in the schematic diagram 400 can power two lasers emitting at the MIR wavelengths of 3 μm, 6 μm, and visible LED of 650 nm. The laser driver is able to change the output power of the multiwavelength lasers through both changing the duty cycle and varying the input current. Everything, in some embodiments, fits into a small (12"×6"×6") 3D casing for a compact physical footprint.

The schematic includes three circuits. The first circuit 402 is a non-inverting op amp voltage amplifier. The op-amp receives 5 V from a microcontroller and outputs 15 V. The gain of this circuit is set by the resistor values of R1 and R2 according to the equation $$A_v = 1 + \frac{R_2}{R_1}.$$

The second circuit 404 contains a LM317 voltage regulator, which in this configuration acts as a constant current supply for our laser. The LM317 has a current output range of 0-1.5 A that can be set by the resistor values between the output and adjustment pins. The total output current can be found using the equation, $$I_{max} = \left(1 + \frac{R_5}{R_4}\right) * \left(\frac{1.25 \; V}{R_3}\right),$$

where $R_5$ is a digital potentiometer that has a variable resistance programmable by the microcontroller. If the digital potentiometer were to fail during operation, the output current is forced low by $R_3$. The current is then defined by, $$I_{min} = \frac{1.25 \; V}{R_3},$$

which with a 40Ω resistor sets the output to 31.25 mA. The minimum current is only slightly above the threshold current of the mid-IR lasers to protect the mid-IR lasers in the event of the electronics failing.

The third circuit 406 is a MOSFET that is connected between the negative terminal of the laser diode and ground. The MOSFET input is a pulsed square wave from the microcontroller, which enables the MOSFET to function as a switch. When the input is high the gate opens, allowing for current to flow through the laser to ground. When the gate is closed, no current flows through the laser, thus turning the laser off. The duty cycle of the laser is controlled by the waveform provided to the gate of the MOSFET, The overall size of the circuit is quite small and can fit into the proposed aluminum casing. The circuit can be powered with an AC-DC 12V power supply.

Figure 5A:
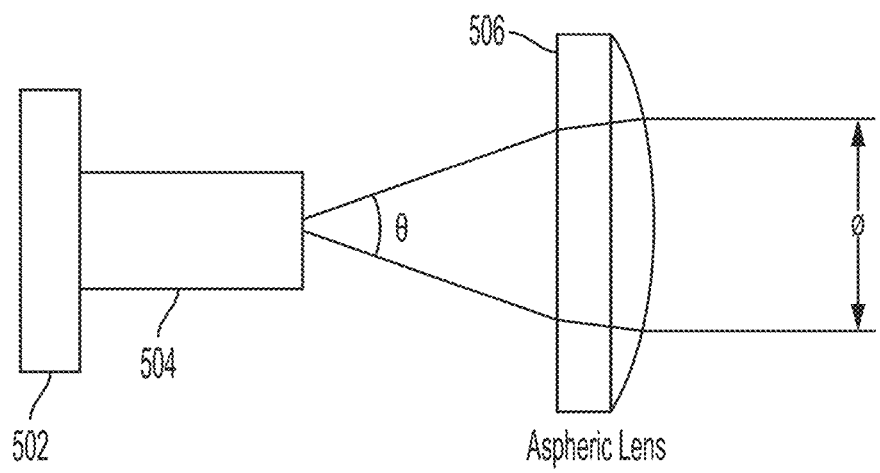
FIG. 5A shows an illustration of a thermoelectric cooler coupled to edge emitting infrared laser diode and an aspheric lens including an antireflection coating, which has a high transmission of mid-infrared radiation, in accordance with some embodiments of the present disclosure.
Figure 5B:
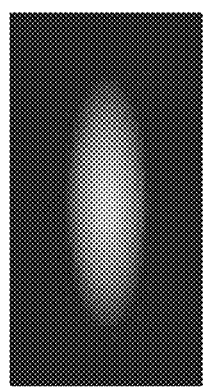
FIG. 5B shows an illustration of an astigmatic beam spot, in accordance with some embodiments of the present disclosure.
Figure 5C:
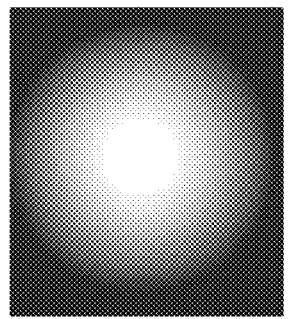
FIG. 5C shows an illustration of the aspheric beam spot, shown in FIG. 5B, after collimation into a circular beam in accordance with some embodiments of the present disclosure.

FIG. 5A shows an illustration of a thermoelectric cooler 502 coupled to edge emitting infrared laser diode 504 and an aspheric lens 506 including an antireflection coating, which has a high transmission of mid-infrared radiation. FIG. 5B shows an illustration of an astigmatic beam spot. Edge emitting lasers typically have astigmatic beam spot because the laser facet is rectangular and diffraction results in a slow- and fast-axis. FIG. 5C shows an illustration of the aspheric beam spot after collimation into a circular beam.

Figure 6:
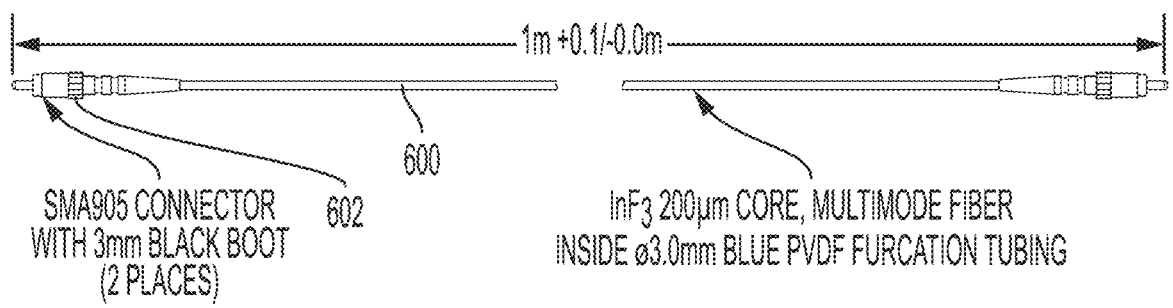
FIG. 6 shows an illustration of a fiberoptic cable in accordance with some embodiments of the present disclosure.
Figure 7:
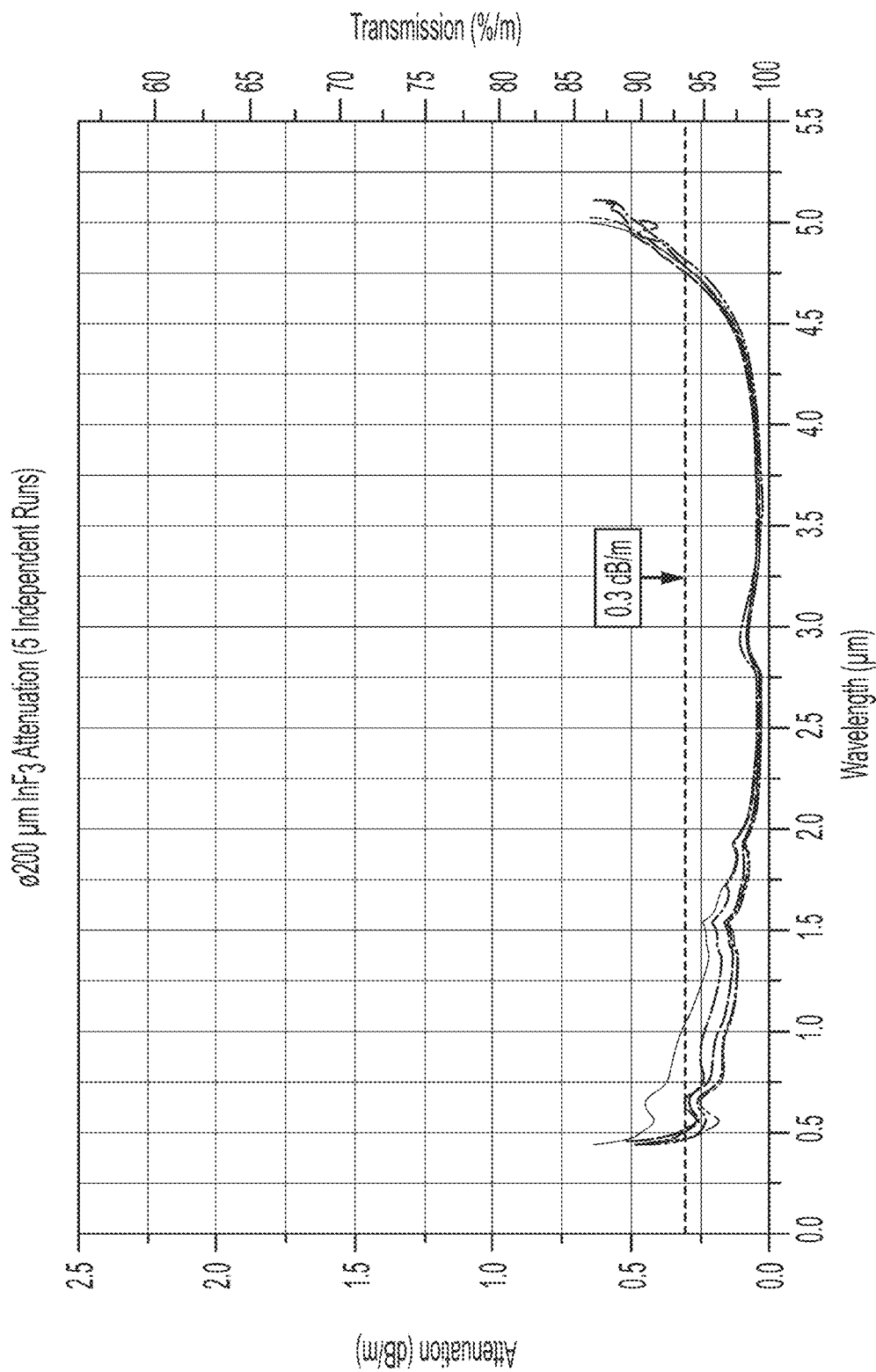
FIG. 7 shows an illustration of a graph of attenuation on the fiberoptic cable shown in FIG. 6 in accordance with some embodiments of the present disclosure.

FIG. 6 shows an illustration of a fiberoptic cable 600 suitable for use with some embodiments of the present disclosure. The fiberoptic cable 600 is a 200-micron core indium fluoride based optical fiber with a PAF2S-11E Fiber-Port coupler and collimator 602 that provides a MIR aspheric lens integrated in the fiberoptic cable 600 to couple and collimate the light out from the MIR laser into a MIR fiber with around 80% coupling efficiency. FIG. 7 shows an illustration of a graph of attenuation in the fiberoptic cable. The fiberoptic cable 600 can be used for fiber-optics based MIR laser scalpel to deliver MIR light to hard to reach surgical areas.

Figure 8:
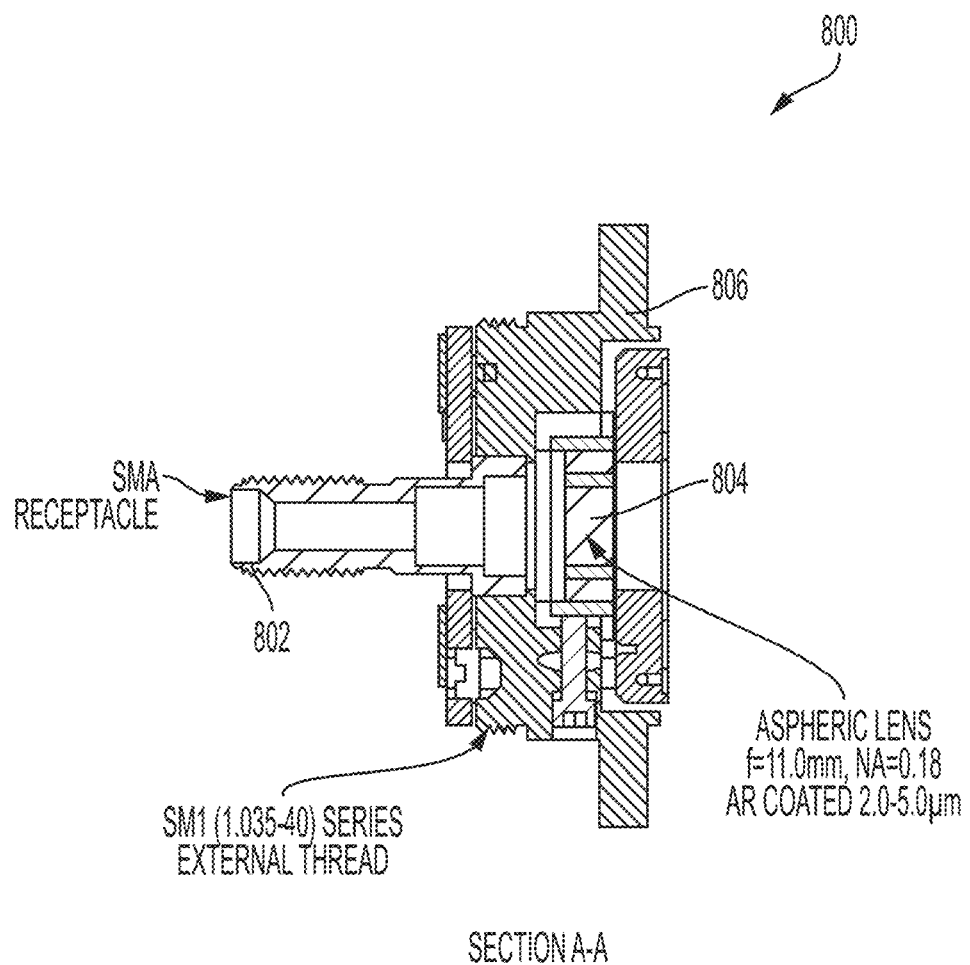
FIG. 8 shows an illustration of laser diode assembly in accordance with some embodiments of the present disclosure.
Figure 9:
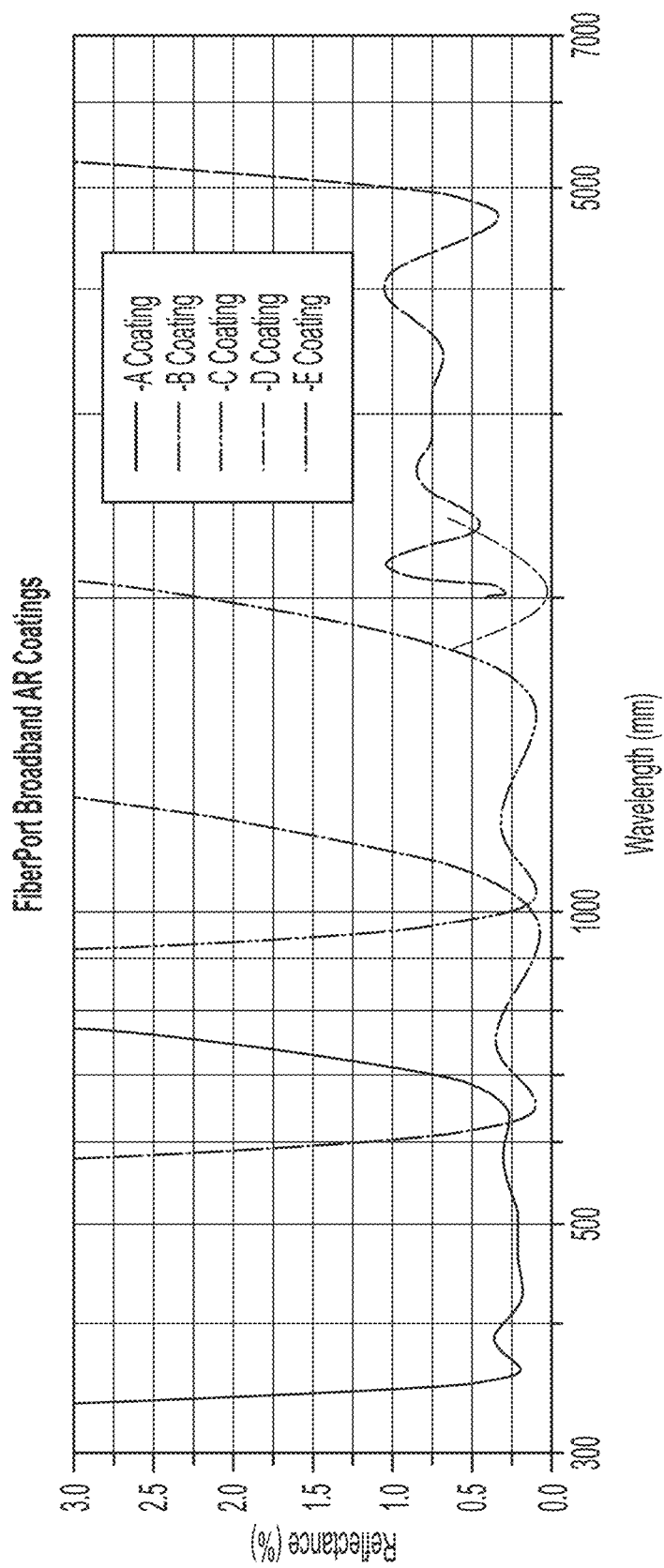
FIG. 9 shows a graph of reflectance of coatings in accordance with some embodiments of the present disclosure.

FIG. 8 shows an illustration of laser diode assembly 800 in accordance with some embodiments of the present disclosure. The laser diode assembly 800 includes an SMA receptacle 802, an aspheric lens 804, and mechanical packaging structures 80610. The depth of the mechanical package is about 26.5 mm. FIG. 9 shows a graph of reflectance of coatings in accordance with some embodiments of the present disclosure.

Example

Mid-infrared (MIR) light refers to wavelengths ranging from 3 to 50 μm and is the most attractive spectral region for ablation of both soft and hard tissues. This is because molecules such as water, proteins, and lipids that are contained in biological tissue exhibit molecular vibrational modes in the MIR wavelengths that result in strong MIR light absorption. Due to the strong MIR light absorption in tissue, substantial heating of small areas is achieved, which enables low collateral thermal damage and very precise excision of biological tissue. MIR also has a relatively shallow absorption depth of 10 to 100 μm compared to near-IR lasers currently used in laser surgeries, which penetrate the tissue at 2000 to 2500 μm. Thus, MIR lasers are not well suited to bulk tumor treatment, but may provide precision ablation after resection of the majority of the tumor by ablating to a shallow absorption depth in remaining tumor beds surrounding sensitive anatomic sites, such as around nerves. Metastatic cancers often invade microscopic, vital, and complex anatomy that is not suitable for largescale resections favored for cancers, such as sarcomas. MIR laser technologies that can precisely damage tissue that could harbor invasive cancer cells may be of value to patients with invasive sarcomas.

Lasers can be used to remove specific structures while preserving surrounding tissue because of their ability to focus radiation into a small area at wavelengths tuned to be selectively absorbed by a given target tissue. According to the American Cancer Society and the National Cancer Institute, the most common lasers used in ablating tumors or activating drugs are carbon dioxide ($CO_2$) lasers ($\lambda$¼ 10.6 µm), argon (Ar) lasers ($\lambda$¼ 350 to 1100 nm), and neodymium:yttrium aluminum garnet (Nd:YAG) lasers ($\lambda$¼ 1064 nm). Notably, none of these common surgical lasers probe the absorption of key tissue components, such as amides and water, which have strong absorption bands around the 3- and 6-µm wavelengths.

Figure 13:
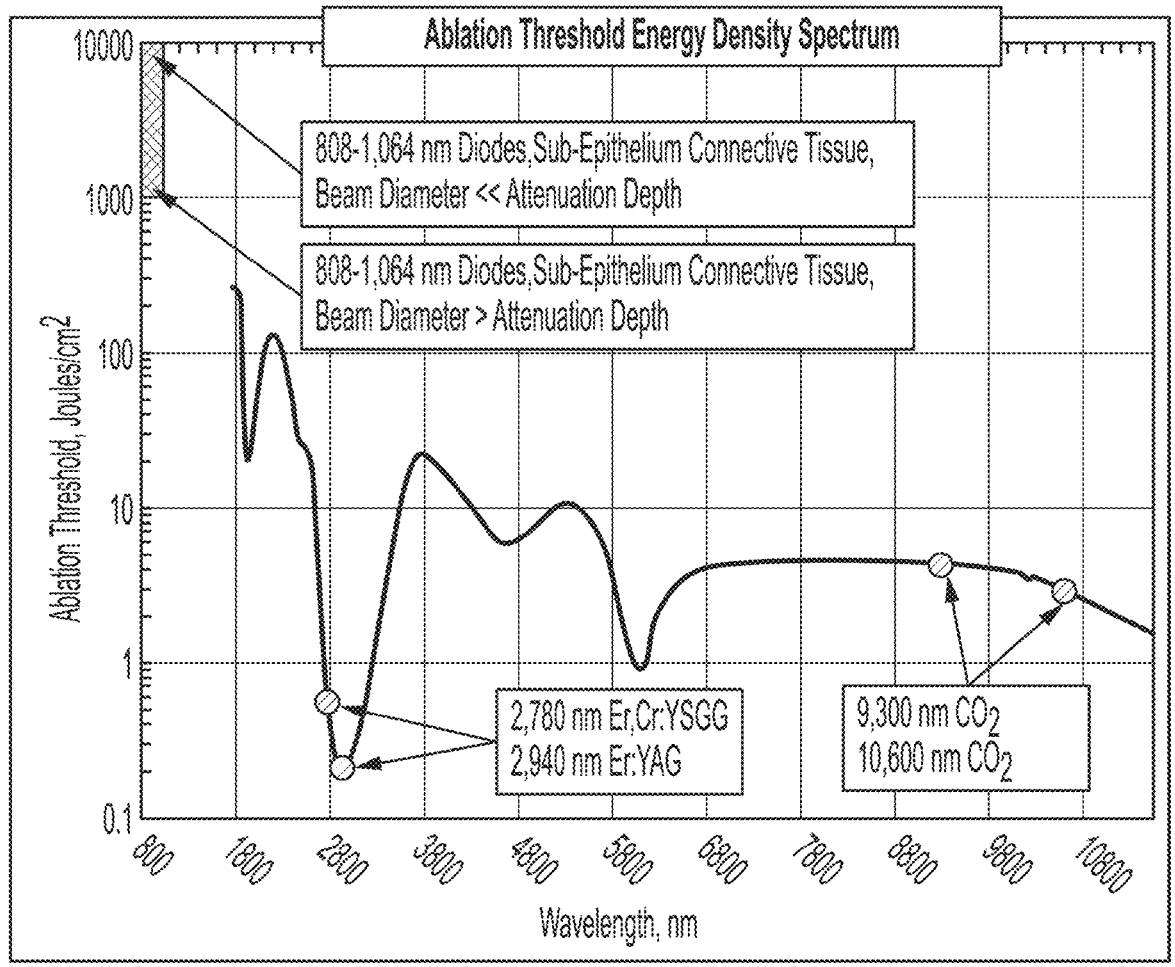
FIG. 13 shows a sub-epithelium/sub-epidermis soft tissue ablation threshold energy density spectrum in accordance with some embodiments of the present disclosure.

The sub-epithelium/sub epidermis soft tissue ablation threshold energy density spectrum, shown in FIG. 13, indicates that around the 3- and 6-µm wavelengths, the ablation threshold is significantly reduced, which means that lasers emitting at these wavelengths are able to effectively ablate soft tissue photothermally at much lower doses than the $CO_2$ lasers, which are the most common surgical lasers on the market today. A primary reason for the low ablation threshold of soft tissue at the 3- and 6-µm wavelengths is that water exhibits strong absorption at these two wavelengths. The high absorption by water at these wavelengths results in extremely short absorption depths (~few microns) in soft tissue, which also enables precise cuts, incision, excision, and coagulation of extremely small tissue volumes with reduced collateral damage.

The data indicates that the use of $\lambda$~3 µm interband cascade laser (ICL) could be highly energy efficient at ablating soft tissues photothermally with very low ablation thresholds. Here, we describe the use of a $\lambda$~3.3-µm interband cascade laser (ICL) that to date has not been used in biomedical applications. ICLs were invented in the 1990s by Professor Rui Yang of the University of Oklahoma and are just now becoming commercially available. The advantages of ICLs include compact size (a few micrometers by a few millimeters), room-temperature operation, and high output power (~0.5 W13). Here, we demonstrate the potential use of ICLs for the development of a compact handheld laser scalpel suitable for a large variety of laser ablative applications.

The use of a $\lambda$~3.3-µm ICL is also strategic for investigating selective ablation of tumor tissue relative to healthy tissue. Other researchers have reported strong absorption of tumor tissue of different cancer types as having a signature absorption around 3.03- to 3.57-µm (or 3300 to 2800 cm-1) wavelength band. This wavelength band is representative of stretching vibration of proteins, such as amide A and amide B, and symmetric and antisymmetric methylene (vs$CH_2$ and vas$CH_2$) stretching bands of lipids and proteins.

We first report on the Fourier transform infrared (FTIR) spectroscopy characterization of six sarcoma patient tissue samples obtained from tumors and surrounding healthy areas to study the molecular-level behavior of the tissues in the MIR wavelengths. Recently, FTIR and Raman spectroscopy approaches have been used to study cancerous specimens in MIR wavelengths, since these vibrational spectroscopic techniques allow for detecting biochemical changes in the blood and tissue samples at molecular level. Through our FTIR measurements, we identify several MIR wavelengths for which cancerous tissue exhibits greater absorbance than healthy tissue. Next, we report on the results obtained using a commercially available ICL with emission wavelength ($\lambda$)~3.3 µm and 30-mW maximum output power, a relatively low-power MIR laser emitting at a wavelength where the ablation threshold is known to be minimum, to probe normal fibroblast and primary undifferentiated pleomorphic sarcoma cell survival after laser exposure. Significant cell death is seen in both groups, but preferential killing of sarcoma cells was not observed. This study demonstrates that ICLs may represent a new avenue toward precise laser ablation.

Tissue Samples for Infrared Spectroscopy

We obtained six myxofibrosarcoma tissue samples from patients banked at the Iowa Residual Tissue Repository through an IRB-approved (ID #: 201512776) Iowa Connective Tissue Proliferative Disorder Clinical Data and Tissue Sample Collection Project. All patients signed an informed consent form before the tissues were collected post-surgery and stored as formalin-fixed paraffin-embedded tissue. Anonymity of the patient data was maintained by removing the HIPAA PHI identifiers. For each patient sample, we obtained a sample of tumor tissue as well as neighboring healthy tissue. Tissues were embedded in paraffin and then sliced to a thickness of 5 µm and mounted on silver (Ag)/tin oxide ($SnO_2$)-coated MIR reflective MirrIR slides (Kevley Technologies, Inc., Ohio) for FTIR measurements. MirrIR slides are recommended for FTIRbased tissue analysis, instead of the traditional glass slides used in optical microscopy analysis, because MirrIR slides have near-perfect MIR reflection and zero MIR transmission, enabling high-quality collection of MIR tissue spectral data. Corresponding tissue samples were mounted on glass slides and then stained with hematoxylin and eosin for optical microscopy examination by a trained and certified pathologist, Dr. Munir Tanas at the University of Iowa Hospitals and Clinics, to confirm the predominant (>65% of tissue) presence of either tumor or normal tissue.

Infrared Spectroscopy

Figure 14:
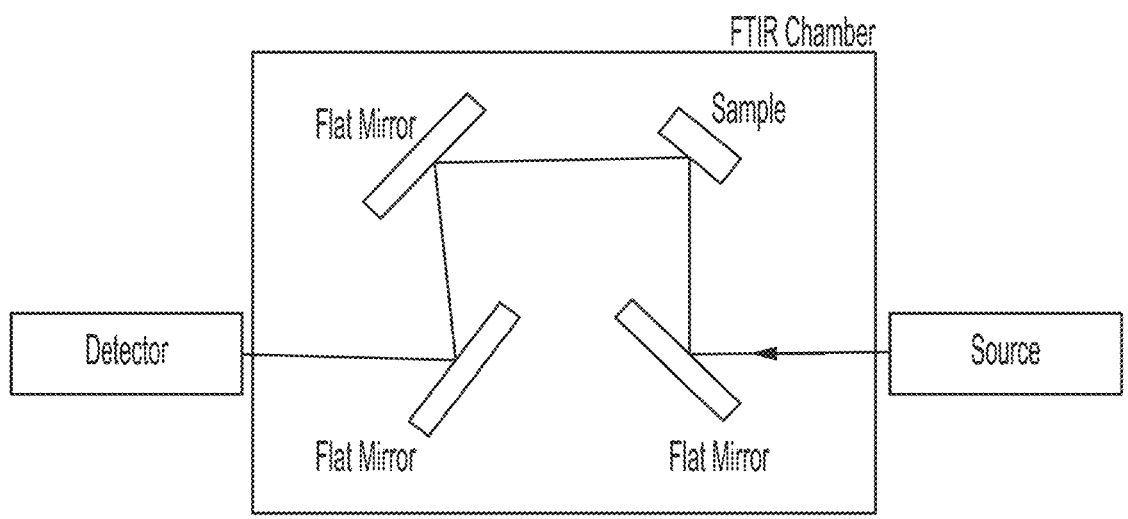
FIG. 14 shows an illustration of a schematic of a mirror and sample arrangement within a FTIR chamber that allowed for specular reflectance measurements of the tissue samples in accordance with some embodiments of the present disclosure.

MIR reflection spectra were collected using an FTIR Nicolet Magna 760 equipped with a mercury cadmium telluride (HgCdTe) liquid nitrogen cooled detector. Spectra were collected in the range of 4000 to 400 cm-1 ($\lambda$¼ 2.5 to 25 µm) with a spectral resolution of 8 cm-1 and with four interferograms averaged. All spectra were collected from samples at room temperature. FIG. 14 illustrates the FTIR chamber with the sample mount and relevant optics utilized to conduct the specular reflectance measurements of the tissue samples mounted on MirrIR slides. We then used the relationship between absorption and reflection, that is, absorption=1−reflection, to obtain the absorption spectra from the measured reflection spectra.

Fibroblast and Cancer Cell Lines

All cell lines were cultured in humidified incubators at 37° C., 5% $CO_2$, 5% and oxygen ($O_2$) to simulate a physiological environment. Cultures were maintained in culture media as follows: 45% DMEM (Dulbecco's modified Eagle medium), 45% F12 nutrient mixture, and 10% fetal bovine serum (all from Gibco, Thermo Fisher Scientific, Inc.). For primary fibroblast cultures, bovine knees were obtained (Bud's Custom Meats, Inc., Iowa), and normal bovine fibroblasts (NBF) were isolated from bovine knee synovia via collagenase/pronase digestions (0.01 mg/ml, Sigma Aldrich, Co.) in serum-free media (50% DMEM, 50% F12) overnight, followed by centrifugation and then plating onto culture flasks. Primary undifferentiated pleomorphic sarcoma tumor cells (C1619) were provided by Dr. Rebecca Dodd.

For laser exposures, all cells were plated into a 96-well microplate (Corning® 96 Well TC-Treated Microplates size 96 wells, polystyrene, flat bottom) with one empty well between each set of test wells to decrease the risk of heating multiple wells at the same time with the laser or accidentally cross contaminating wells. The cell lines were plated separately on 96-well dishes and grown to an equal confluency prior to exposure of 80% to 90%. This high confluency was used to minimize differences in cell cycle distribution between the two cell lines, which grow at very different rates. Cell counts were confirmed using a hemocytometer.

Laser Exposure

Figure 15A:
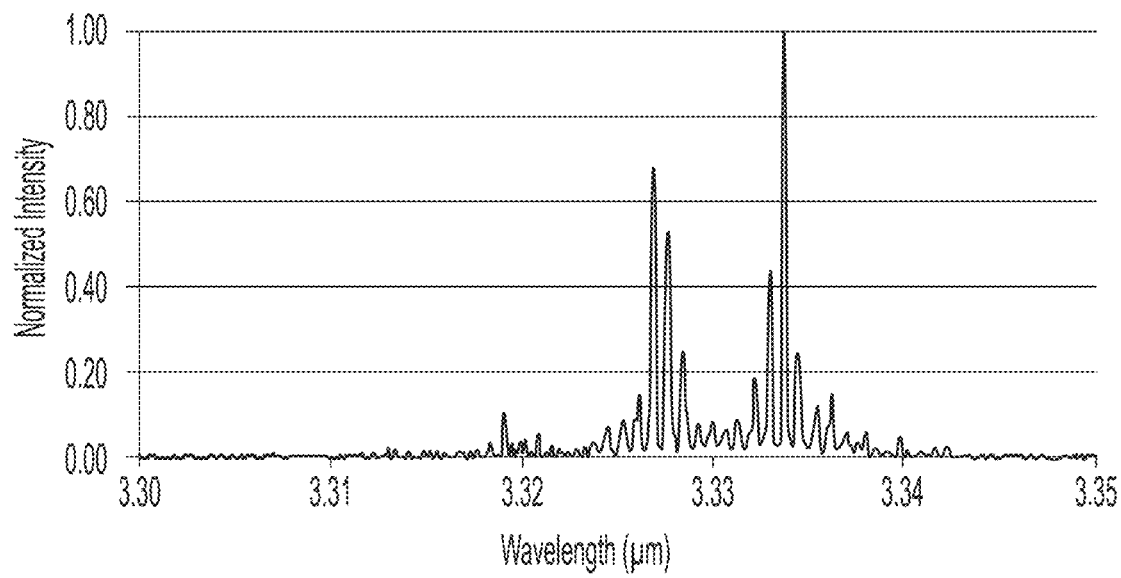
FIG. 15A shows an emission spectrum measured at an injection current of 448 mA in accordance with some embodiments of the present disclosure.
Figure 15B:
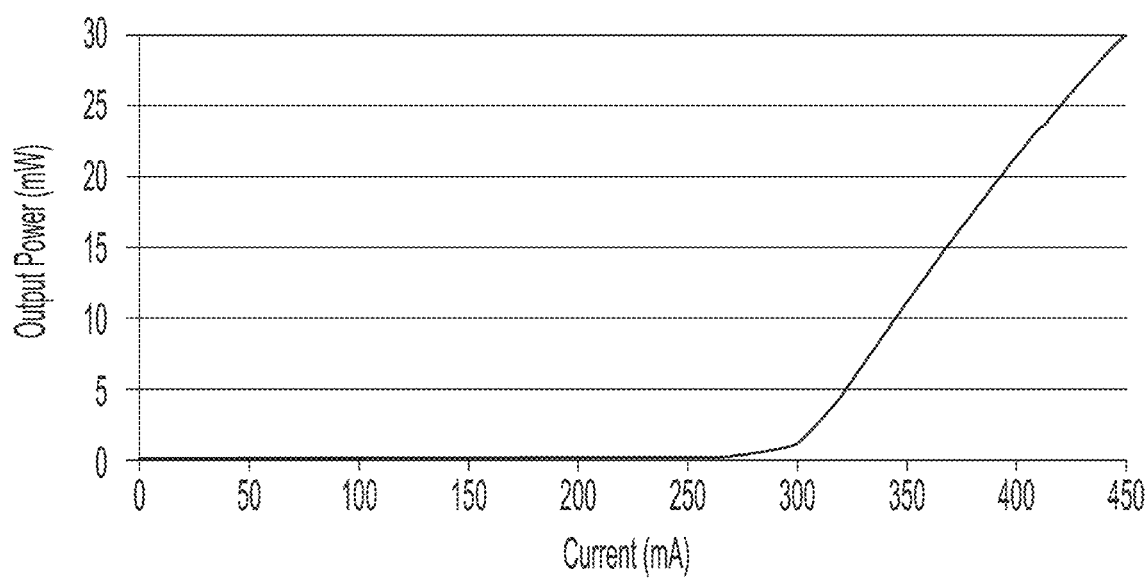
FIG. 15B shows light-current characteristics a λ~3.3 µm Fabry-Perot ILC in used in measurements in accordance with some embodiments of the present disclosure.

A λ~3.3-μm Fabry-Perot ICL (IF3300CM2, Thorlabs, Inc., New Jersey) was used for these studies. The representative emission spectrum and light-current curve of the ICL are shown in FIG. 15A and FIG. 15B, which confirms that the laser emission is centered at 3.33 μm 0.01 μm and has a maximum power output of 30 mW, which corresponds to 93.75 mW/cm$^2$ of irradiance as defined by the 0.32-cm$^2$ area of the microwells in which the cells were hosted. The MIR ICL was mounted on a temperature-controlled LDMC20 laser mount from Thorlabs. The laser was operated using Thorlabs' ITC4000 Laser Diode Current and Temperature Controller. The faceplate of the LDMC was removed during exposures to minimize the distance from the laser to the cells. The laser was thermoelectrically cooled (TEC) to 15° C. using the ITC4000 temperature controller and maintained at this temperature throughout the cell line exposure experiments to maintain constant laser power across experiments.

Immediately prior to laser radiation exposure, 96-well microplates were removed from the incubator and culture media was removed from individual wells to prevent absorption by media. After ICL MIR radiation exposures, 100 μl of media was returned to each well. To determine the possible impact of 21% ambient oxygen exposure on the cells in the microplate wells during laser exposure, six control wells with media removed for 180 s but with no laser exposure were included in each microplate. Microplate wells populated with cells but with no media removal were also included.

Individual plates had three samples of each cell type for each laser exposure time. The 30-, 60-, and 90-s samples were radiated on one plate while the 180-s trials were done on a plate that was still in the incubator while the first plate was being exposed to reduce the amount of time the cells were out of the incubator. After completion of all laser exposures, 100 μl of serum-free media with no phenol red was added to each well and the dish was returned to the incubator for 1 h prior to cell viability measurements.

Automation of Laser Exposure

Figure 10:
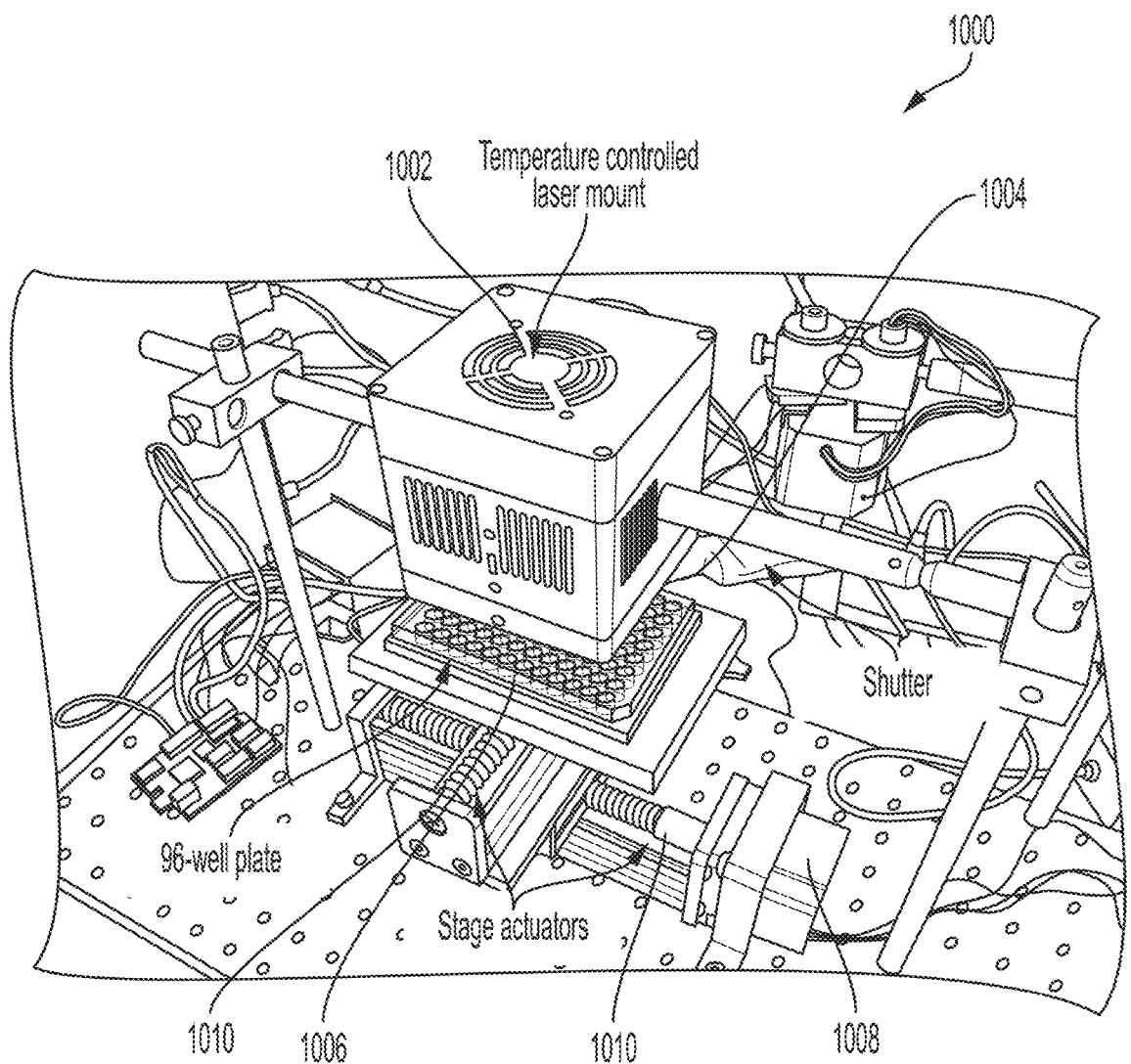
FIG. 10 shows an illustration of a photograph showing a temperature-controlled laser mount, the 3D-printed shutter, a 96-well microplate placed on a stage, driver motors, and stage actuators in accordance with some embodiments of the present disclosure.
Figure 16:
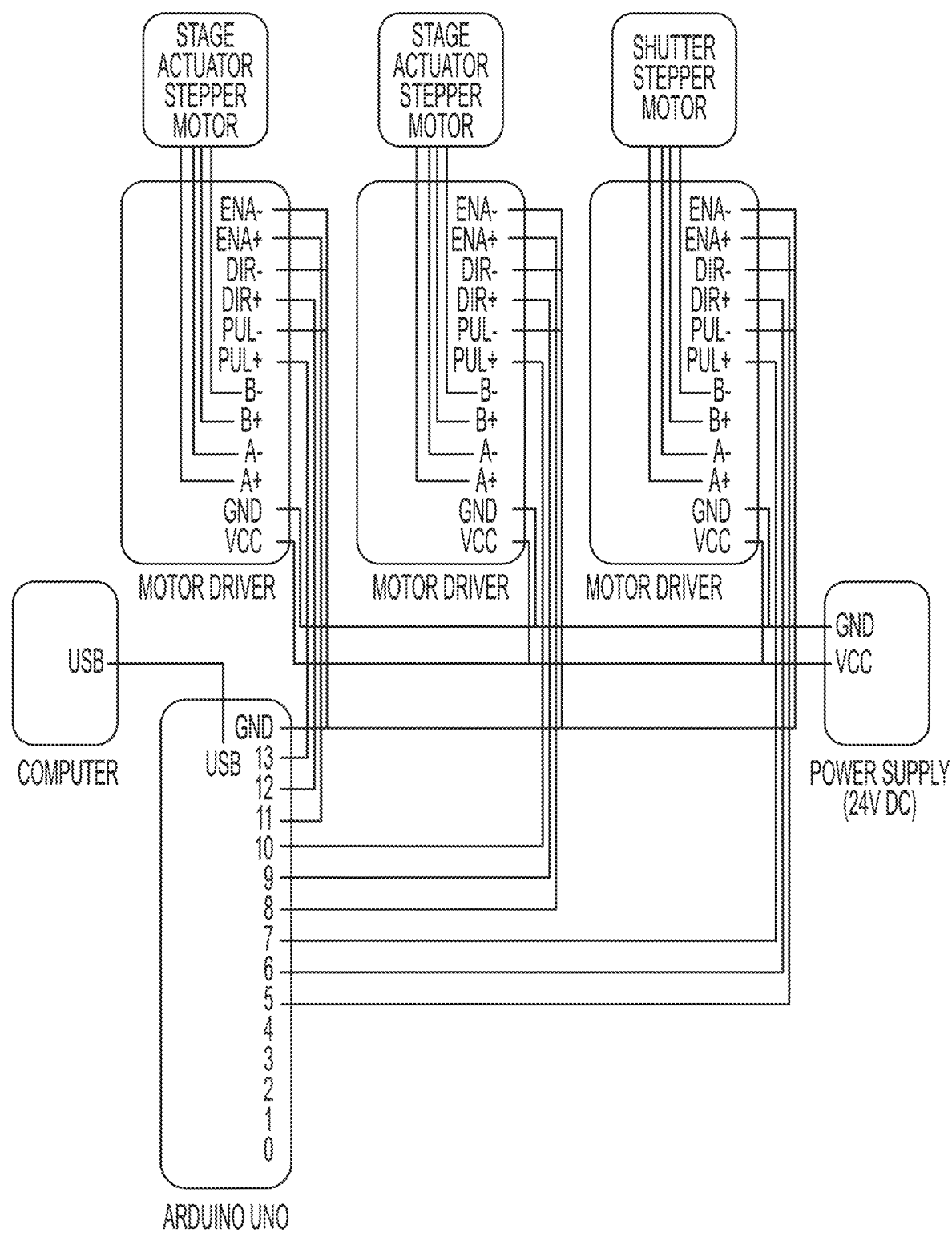
FIG. 16 shows a block diagram of circuit elements and electrical connections for a automated shutter and stage in accordance with some embodiments of the present disclosure.

To ensure accurate laser exposure times, we developed a computer-controlled shutter system using 3D-printed components from our lab. This system allowed us to automate the opening and closing of the shutter for precise periods of time as well as to move the stage on which the 96-well microplate was placed an exact distance with respect to the laser mount. The shutter system also allowed us to keep the ICL powered up and maintained at a constant temperature of 15° C. throughout the experiments, which alleviated any variations in the ICL's MIR light output. FIG. 10 shows an illustration of a photograph showing a shutter system 1000 including a temperature-controlled laser mount 1002, the 3D-printed shutter 1004, a 96-well microplate 1006 placed on a stage, driver motor 1008, and stage actuators 1010 in accordance with some embodiments of the present disclosure. The shutter system 1000 included of two linear stage actuators controlled by two motor drivers and a third motor driver to control a shutter connected to an Arduino Uno. The Arduino Uno was connected via USB to a workstation during the experiment, and the shutter and stage actuators were controlled via a serial input. We wrote Python script to control and operate the shutter and the stage on which the 96-well microplate was placed. FIG. 16 shows the block diagram for the microcontroller and the motors circuitry.

The shutter was used to control ICL laser exposure times accurately. While the laser was kept on at all times and maintained at a constant temperature through the TEC controller, the shutter opened or closed for desired periods of time to expose or cover each microplate well. After a specific microplate well received the appropriate laser exposure, the stage upon which it was placed was moved precisely using the automated stage actuators.

It is important to note that the 3D-printed shutter was made of acrylonitrile butadiene styrene (ABS), which is absorbed by the 3.3-μm laser output and was effective in blocking the laser light from reaching the wells when the shutter was closed. Moreover, the 96-well plate was made of polystyrene which also absorbs 3.3-μm laser radiation; therefore, the laser output did not penetrate the cells in the adjacent wells through the sides of the wells. We confirmed the 100% absorption of the 3D-printed ABS-based shutter and polystyrene microplate at 3.3-μm MIR wavelength using the FTIR in our lab.

MTS Assay

To assess cell viability after laser exposures, we used the 3-(4,5-dimethylthiazol-2-yl)-5-(3-carboxymethoxyphenyl)-2-(4-sulfophenyl)-2H-tetrazolium (MTS) assay (Abcam plc, Massachusetts). This assay relies upon dye uptake, subsequent reduction, and retention in live cells that does not occur within dead cells. This absorbance is measured at 490 nm and conducted in the same 96-well microplate in which the cells were exposed to laser radiation. One hour after laser exposure, we added 10 μl of the MTS reagent to 100 μl of media already within the wells and then returned the plate to the incubator. ATECAN plate reader read absorbance at 490 nm. We also measured the absorbance of three wells with reagents without cells as controls. We averaged the absorbance of each set of wells exposed to a specific laser radiation dose and subtracted these values from the average of the no-cell control wells to compare the absorbance resulting from different laser doses.

Confocal Microscopy

For confocal microscopy images of normal and exposed cells, we plated 20,000 cells per well of a two-well chamber slide. We aspirated the porcine media from each chamber immediately before exposure, exposed the center of each chamber to a laser at 17 mW for 90 s (1.5 J of energy), and then re-added media to the chamber as rapidly as possible. One hour after exposure, we aspirated the media from all wells to remove debris, then added the viability dye Calcein AM (4 μM) and the dead cell stain ethidium homodimer (2 μM) (both from Life Technologies, Thermo Fisher, Inc.) for 30 min in serum-free and phenol-red-free culture medium. Cells were then imaged with an Olympus FV1000 confocal microscope at a total magnification of 40× (4×objective), centered on the site of exposure.

Histopathology of Healthy and Sarcoma Tissues

Given the heterogeneity of the sarcoma cancer tissue, we tested six different patient samples to determine the absorption profile of healthy versus cancerous tissues of each sample. FIG. 18 shows a patient Table including patient demographics, diagnosis, type of tissue, and anatomical location the cancer in accordance with some embodiments of the present disclosure. The sample set had gender diversity as well as anatomical location variation. However, the diagnosis was similar for all patients, myxofibrosarcoma.

Figure 17:
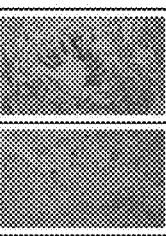
FIG. 17 shows optical microscope images of normal and tumor tissues for the six patients measured using tissues mounted on traditional glass slides in accordance with some embodiments of the present disclosure.

We collected optical microscopy images of the healthy and cancerous tissue samples. FIG. 17 shows optical microscope images of normal and tumor tissues for the six patients measured using tissues mounted on traditional glass slides in accordance with some embodiments of the present disclosure. A green filter was used for the image collection, which resulted in the green background. Since the analysis of these images was to be qualitative, the use of the filter did not impact our analysis. The comparison of the optical images confirms a distinct difference between healthy and cancerous tissues as expected. Cancerous tissues clearly have the cell structure completely disrupted while it is well maintained in the neighboring healthy tissue samples. The optical microscopy analysis was primarily qualitative to confirm the structural differences in cancerous and healthy tissue samples.

Next, we conducted FTIR reflection measurements of the healthy and cancerous tissue samples mounted on MirrIR slides using the setup shown in FIG. 14. FIG. 14 shows an illustration of a schematic of a mirror and sample arrangement within a FTIR chamber that allowed for specular reflectance measurements of the tissue samples in accordance with some embodiments of the present disclosure. One MirrIR slide had just the mounting media, the IR spectra of which was also measured and subtracted from the tissue spectra.

Figure 11:
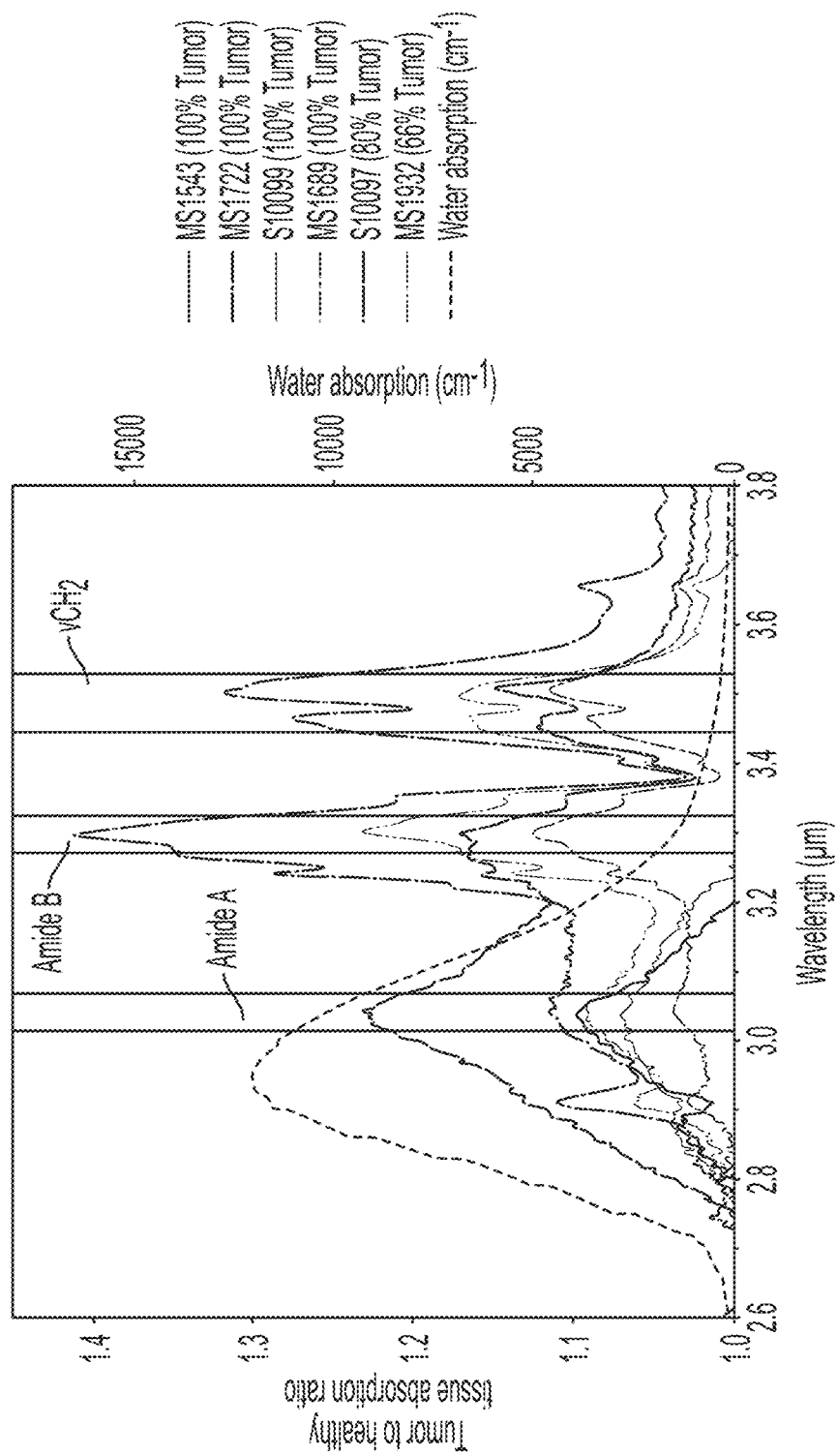
FIG. 11 shows a MIR spectra of tumor to healthy tissue absorption ratio (left y-axis) obtained from the analysis of FTIR measurements for the wavelengths of 2.6 to 3.8 µm in accordance with some embodiments of the present disclosure.

FIG. 11 shows the post-processed spectral data of the tumor to healthy tissue absorption ratio as a function of wavelength. The tissue ratio spectra are overlaid on the water absorption spectra in FIG. 11 to confirm that none of the tissue spectra features are due to water absorption, which has a strong absorption band near 3-μm wavelength. Ratio of 1 represents equal MIR absorption in tumor and healthy tissues and any ratio value larger than 1 indicates higher absorption in tumor tissue relative to healthy tissue at that specific MIR wavelength. Overall, FIG. 11 indicates that all six tumor tissues exhibit higher MIR absorption than their neighboring healthy tissue, as indicated by the higher than 1 absorption ratio around the 3- to 3.5-μm MIR wavelengths. Furthermore, there are three specific absorption bands that stand out in the spectral data due to their high absorption magnitude. Three spectral regions are highlighted to represent the relevant stretching vibration groups of tissue proteins: amide A (blue-shaded region), amide B (green-shaded region), and methylene ($\upsilon CH_2$) (red-shaded region).

The first absorption band at ~3.035 μm (or 3295 cm$^{-1}$) is representative of the stretching vibration of amine ($\nu NH$) groups of proteins and indicates that the protein formulation is in the form of amide A, as previously shown by others. The second absorption band at ~3.295 μm (or 3034.90 cm$^{-1}$) indicates that the tissue proteins also have the configuration of amide B. In the case of amide B, the β-sheet protein structure predominates, which means that the effect of the NH group of the peptide bond —NHCO— is stronger than C=O, unlike in amide A, where the effect of C=O in the peptide bond is stronger. The third absorption band around 3.450 to 3.530 μm (or 2900 to 2830 cm$^{-1}$) is representative of symmetric and antisymmetric methylene ($\nu_s CH_2$ and $\nu_{as} CH_2$) stretching bands of lipids and proteins. Notably, these three absorption bands have been reported to be dominant in different cancer type tissues.

The heterogeneity of the tissue structure for each of the patients in FIG. 11 is apparent in the MIR absorption spectra, where the absorption ratio across 2.8 to 3.6 μm varies for each sample. For example, in patient samples S10099 and MS1543, the tumor tissues exhibit higher absorption than neighboring healthy tissues, only for the amide A band. From the optical microscopy images of the tumor tissues for these two patient samples, shown in FIG. 17 it is evident that the cell structure is rather sparse in the tumor tissues for both cases. For patient sample S10097, tumor tissue exhibits higher absorption in the amide A band than the amide B band, while for patient samples MS1722, MS1932, and MS1689, absorption in the amide B band is higher than in the amide A band. The coexistence of both A and B protein conformations illustrates the prevalence of different hydrogen bonds that hold the protein strands together. It is known that the hydrogen bond is important in stabilizing the protein helix and that any change implies that the physiological environment has changed. Several researchers have demonstrated that these changes in hydrogen bonds are important in characterizing disease and its progression. Finally, the FTIR spectral analysis enabled us to select an ICL emission wavelength of λ~~3.3-μm laser that would be effective in ablating tumor tissue selectively.

Cell Viability Analysis of ICL-Exposed Cell Lines

To study the duration of exposure to ICL radiation needed to kill cells cultured in a monolayer, we used the maximum power output of 30 mW from the λ~3.3-μm ICL. With the microplate well surface area of 0.32 cm$^2$, this corresponds to 93.75 mW/cm$^2$ of irradiance. Both the C1619 and NBF cell lines were exposed to the 3.3-μm laser radiation. Three different exposure times were chosen: 30, 90, and 180 s, which corresponds to 2.81, 8.44, and 16.87 J/cm$^2$ of radiant exposure, respectively. FIG. 3(a) shows the absorbance data of both cell lines using the MTS assay measured using the TECAN plate reader and normalized to control wells receiving no laser radiation. Data confirm that 30-mW laser radiation at a 3.3-μm emission wavelength can kill up to 50% of cells effectively with p<0.05 via two-way ANOVA. No statistical difference is found between the mortality rate of the two cells types after normalization.

Figure 12A:
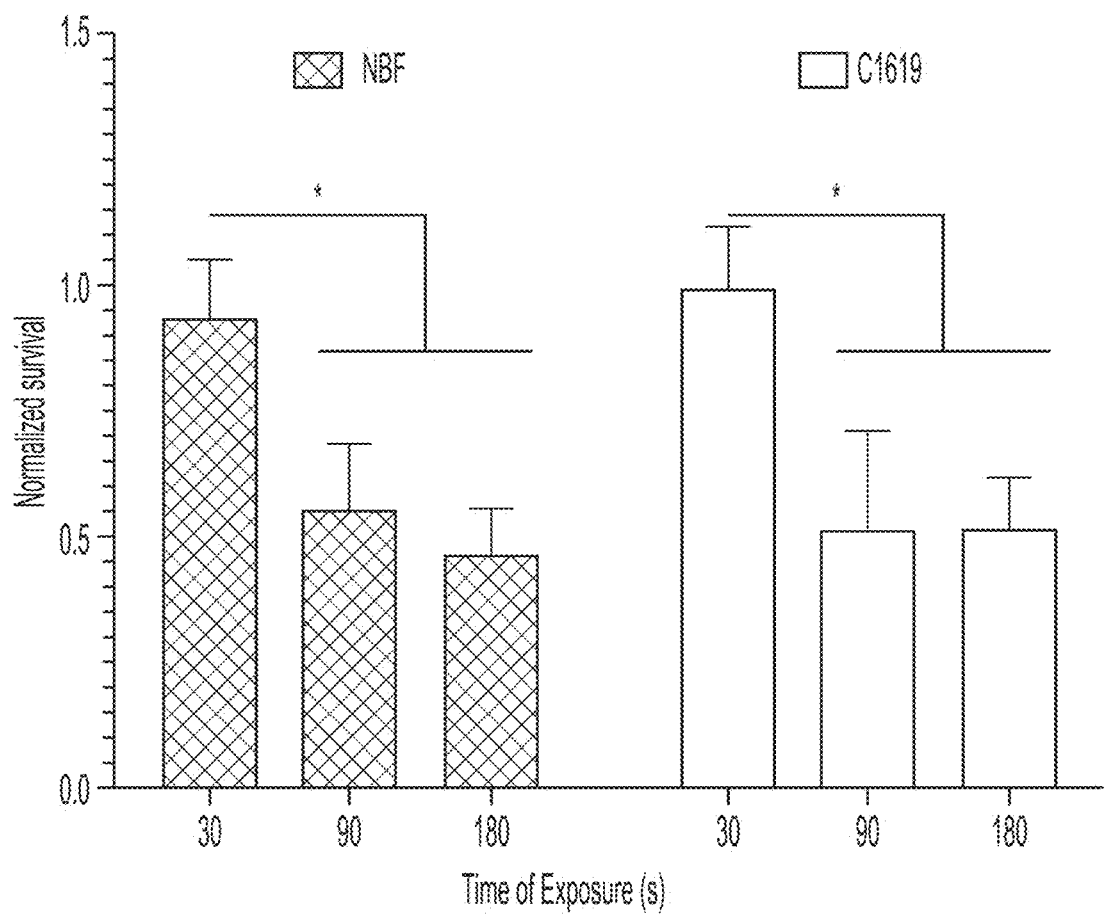
FIG. 12A shows a comparison of cell death for NBF and C1619 cells after 30-mW power, 3.3-µm ICL radiation for three different exposure times, 30, 90, and 180 s in accordance with some embodiments of the present disclosure.
Figure 12B:
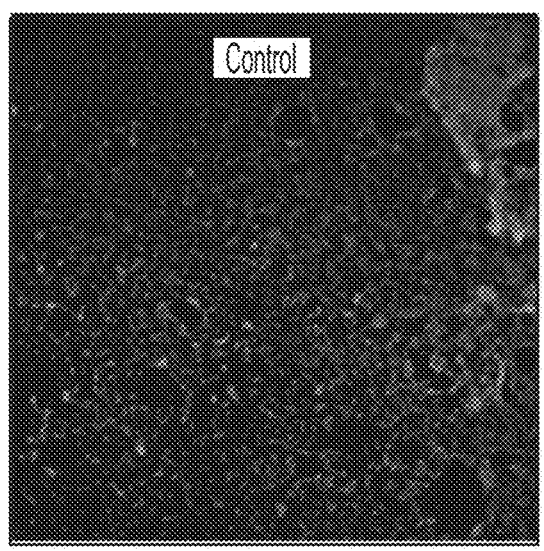
FIG. 12B shows Calcein AM live cells in accordance with some embodiments of the present disclosure.
Figure 12C:
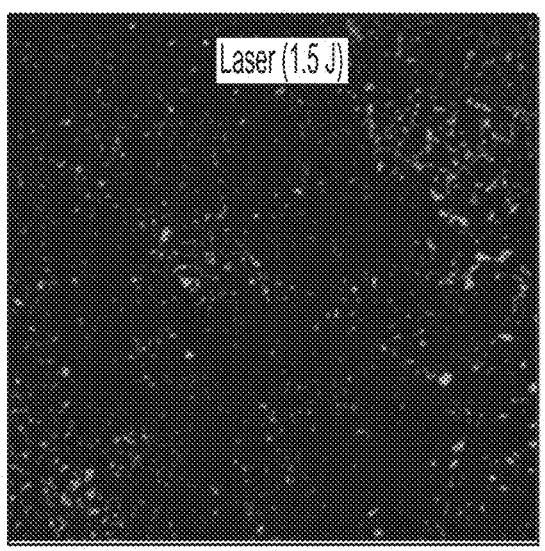
FIG. 12C shows ethidium homodimer red dead cell in accordance with some embodiments of the present disclosure.

To confirm changes in cell viability, we performed confocal microscopy on cultures of cells stained with Calcein AM to indicate live cells and ethidium homodimer to indicate dead cells. FIG. 12B shows a representative confocal microscopy image of the cell culture with no laser radiation exposure and FIG. 12C represents an image after exposure to 1.5 J of laser radiation. We note very little ethidium homodimer staining and an apparent lack of cellular material in FIG. 12C. Combined with the short duration of the experiment, this suggests that cellular material had lifted off of the plates or rinsed away during staining, and implicates a necrotic cell death rather than more regulated forms of death.

These data suggest that, while FTIR identified 3.3 μm as a promising candidate, this wavelength did not provide preferential killing of cultured cancer cells over normal cells or any differential effect with MIR lasers. This lack of differential killing could be related to the culture system utilized, i.e., differences in FTIR absorbance observed may be related to tissue composition and not inherent differences of cancer cells relative to normal cells. In addition to potential differences in composition of the surrounding extracellular matrix itself, tumors also possess erratic and at times very poor blood supplies, and these differences may explain our FTIR result. Nonetheless, the power levels used in this experiment to ablate cancer and normal cells were very low and resulted in significant cell death at sites of exposure. This may prove therapeutically valuable in specific settings where shallow penetration of small areas is needed, such as within tumor beds that remain after resection around sensitive structures.

In this work, we present FTIR characterization of sarcoma and healthy tissues obtained from six patients of diverse demographic backgrounds but similar diagnoses. We demonstrate that the absorption of tumorous tissue is higher than neighboring healthy tissue around 3-μm MIR wavelengths, specifically in the amide A, amide B, and methylene absorption bands. Using this data, we then conduct studies on a cancer cell line (C161fluior9) to study the efficacy of a relatively low power (30 mW) ICL in ablating cell lines. We confirm cell death after ICL radiation exposure using MTS assay and confocal microscopy analysis.

In the preceding specification, various example embodiments have been described with reference to the accompanying drawings. It will, however, be evident that various modifications and changes can be made thereto, and additional embodiments may be implemented based on the principles of the present disclosure. The specification and drawings are accordingly to be regarded in an illustrative rather than restrictive sense.

For example, advantageous results still could be achieved if steps of the disclosed techniques were performed in a different order or if components in the disclosed systems were combined in a different manner or replaced or supplemented by other components. Other implementations are also within the scope of the following example claims.

What is claimed is:

1. A method of treatment of an animal comprising:
   activating a visible targeting beam in a laser scalpel, the visible targeting beam having an illumination intensity, the laser scalpel having a compact form factor and includes a milli-watt power mid-infrared quantum cascade laser;
   illuminating a tumor that includes undifferentiated pleomorphic sarcoma cancer cells and non-cancerous cells with the visible targeting beam;
   activating the invisible milli-watt power mid-infrared laser scalpel to produce a laser spot at the tumor;
   operating the invisible milli-watt power mid-infrared quantum cascade laser at a temperature of about 15° C.; and
   ablating the undifferentiated pleomorphic sarcoma cancer cells while leaving the non-cancerous cells substantially undamaged.

2. The method of claim 1, further comprising:
   operating the invisible milli-watt power mid-infrared laser at a duty cycle of between about 0.1 percent and about 1 percent at a frequency of between about one hundred hertz and about one kilohertz.

3. The method of claim 2, further comprising:
   activating a predefined tumor exposure profile to control the invisible milli-watt power mid-infrared laser that fits into a small 3D casing for the laser scalpel.

4. The method of claim 3, wherein activating the milli-watt power invisible mid-infrared laser to produce the laser spot at the tumor comprises activating an interband cascade laser having width of between about two and about five millimeters, a thickness of about ten micrometers and a width of about ten micrometers.

* * * * *